United States Patent
Liu et al.

(10) Patent No.: US 10,688,105 B2
(45) Date of Patent: Jun. 23, 2020

(54) METHOD OF TREATING REFRACTORY RHEUMATOID ARTHRITIS ASSOCIATED WITH P53 MUTATION

(71) Applicant: Macau University of Science and Technology, Taipa (MO)

(72) Inventors: Liang Liu, Taipa (MO); Kam Wai Wong, Taipa (MO); Yuen Kwan Law, Taipa (MO); Cong Ling Qiu, Taipa (MO)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 0 days.

(21) Appl. No.: 15/644,945

(22) Filed: Jul. 10, 2017

(65) Prior Publication Data

US 2019/0008872 A1    Jan. 10, 2019

(51) Int. Cl.
*A61K 31/185*    (2006.01)
*A61K 31/495*    (2006.01)
(Continued)

(52) U.S. Cl.
CPC ............ *A61K 31/56* (2013.01); *A61K 31/165* (2013.01); *A61K 31/19* (2013.01); *A61K 31/365* (2013.01);
(Continued)

(58) Field of Classification Search
CPC ...................................................... A61K 31/192
(Continued)

(56) References Cited

U.S. PATENT DOCUMENTS 5,294,443 A * 3/1994 Lipsky ................. A61K 31/365
424/759

FOREIGN PATENT DOCUMENTS

AU    2015101808 A4 *  2/2016
CN    1011548950 A  * 10/2009

OTHER PUBLICATIONS

Gan et al. "Celastrol Attenuates bone erosion in collagen-induced arthritis mice and inhibits osteoclast differentiation and function in RANKL-induced RAW264.7," International Immunopharmacology, 2015, vol. 24, pp. 239-246.*

(Continued)

*Primary Examiner* — Shengjun Wang
(74) *Attorney, Agent, or Firm* — Renner Kenner Greive Bobak Taylor & Weber

(57) ABSTRACT

A method for treating a subject suffering from refractory rheumatoid arthritis includes the step of administering an effective amount of a quinonemethide triterpenoid or a pharmaceutically tolerable salt, solvate or anhydrate thereof to the subject. Also is a method for inducing autophagy in a synovial fibroblast, and a method of inducing calcium mobilization in a synovial fibroblast. Further a pharmaceutical composition includes an effective dose of a quinonemethide triterpenoid and an anti-arthritis compound. The quinonemethide triterpenoid is suitable to treat refractory rheumatoid arthritis (RA) in particular ABC-protein-dependent RA and apoptosis-deficient RA. The quinonemethide triterpenoid also possesses significant inhibitory effects on the growth of synovial fibroblasts, in particular modulating the calcium homeostasis in multidrug-resistant rheumatoid arthritis synovial fibroblasts.

11 Claims, 24 Drawing Sheets

Specification includes a Sequence Listing.

(51) Int. Cl.
| | |
|---|---|
| A61K 31/56 | (2006.01) |
| A61K 31/519 | (2006.01) |
| A61K 31/573 | (2006.01) |
| A61K 31/165 | (2006.01) |
| A61K 31/42 | (2006.01) |
| A61K 45/06 | (2006.01) |
| A61K 31/635 | (2006.01) |
| A61K 31/19 | (2006.01) |
| A61K 39/00 | (2006.01) |
| A61K 31/365 | (2006.01) |

(52) U.S. Cl.
CPC ............ *A61K 31/42* (2013.01); *A61K 31/519* (2013.01); *A61K 31/573* (2013.01); *A61K 31/635* (2013.01); *A61K 39/00* (2013.01); *A61K 45/06* (2013.01)

(58) Field of Classification Search
USPC .................................................. 514/577, 249
See application file for complete search history.

(56) References Cited

OTHER PUBLICATIONS

Xu et al. "Celastrol induced DNA damage, cell cycle arrest, and apoptosis inhuman rheumatoid fibroblast-like synovial cells," American Journal of Chinese Medicine, 2013, vol. 41, No. 3, pp. 615-618, CAplus Abstract, CN 2013:852960.*

Xu et al. Celastrol induced DNA damage, cell cycle arrest, and apoptosis inhuman rheumatoid fibroblast-like synovial cells, American Journal of Chinese Medicine, 2013, vol. 41, No. 3, pp. 615-618. (Year: 2013).*

Sun et al. "p53, Proto-oncogene and Rheumatoid Arthritis", Seminars in Arthritis and Rheumatism, 2002, vol. 31, No. 5, pp. 299-310. (Year: 2002).*

Maillefert JF, Maynadie M, Tebib JG, Aho S, Walker P, Chatard C, et al. Expression of the multidrug resistance glycoprotein 170 in the peripheral blood lymphocytes of rheumatoid arthritis patients. The percentage of lymphocytes expressing glycoprotein 170 is increased in patients treated with prednisolone. Br J Rheumatol 1996;35:430-5.

Jiang M, Zha Q, Zhang C, Lu C, Van X, Zhu W, et al. Predicting and verifying outcome of Tripterygium wilfordii Hook F. based therapy in rheumatoid arthritis: from open to double-blinded randomized trial. Sci Rep 2015;5:9700.

Tao X, Lipsky PE. The Chinese anti-inflammatory and immunosuppressive herbal remedy Tripterygium wilfordii Hook F. Rheum Dis Clin North Am 2000;26:29-50, viii.

Lv QW, Zhang W, Shi Q, Zheng WJ, Li X, Chen H, et al. Comparison of Tripterygium wilfordii Hook F with methotrexate in the treatment of active rheumatoid arthritis (TRIFRA): a randomised, controlled clinical trial. Ann Rheum Dis 2015;74:1078-86.

Venkatesha SH, Yu H, Rajaiah R, Tong L, Moudgil KD. Celastrus-derived celastrol suppresses autoimmune arthritis by modulating antigen-induced cellular and humoral effector responses. J Biol Chem 2011;286:15138-46.

Nanjundaiah SM, Venkatesha SH, Yu H, Tong L, Stains JP, Moudgil KD. Celastrus and its bioactive celastrol protect against bone damage in autoimmune arthritis by modulating osteoimmune crosstalk. J Biol Chem 2012;287:22216-26.

Li G, Liu D, Zhang Y, Qian Y, Zhang H, Guo S, et al. Celastrol inhibits lipopolysaccharide-stimulated rheumatoid fibroblast-like synoviocyte invasion through suppression of TLR4/NF-kappaB-mediated matrix metalloproteinase-9 expression. PLoS One 2013;8:e68905.

Li GQ, Zhang Y, Liu D, Qian YY, Zhang H, Guo SY, et al. Celastrol inhibits interleukin-17A-stimulated rheumatoid fibroblast-like synoviocyte migration and invasion through suppression of NF-kappaB-mediated matrix metalloproteinase-9 expression. Int Immunopharmacol 2012;14:422-31.

Astry B, Venkatesha SH, Laurence A, Christensen-Quick A, Garzino-Demo A, Frieman MB, et al. Celastrol, a Chinese herbal compound, controls autoimmune inflammation by altering the balance of pathogenic and regulatory T cells in the target organ. Clin Immunol 2015;157:228-38.

* cited by examiner

METHOD OF TREATING REFRACTORY RHEUMATOID ARTHRITIS ASSOCIATED WITH P53 MUTATION

SEQUENCE LISTING

The Sequence Listing file entitled "sequencelisting" having a size of 609 bytes and a creation date of 10 Jul. 2017 that was filed with the patent application is incorporated herein by reference in its entirety.

TECHNICAL FIELD

The present invention relates to a method of treating rheumatoid arthritis, in particular refractory rheumatoid arthritis, via administration of a quinonemethide triterpenoid. The present invention also relates to a pharmaceutical composition comprising the quinonemethide triterpenoid and an anti-arthritis compound, in particular for treatment of refractory rheumatoid arthritis.

BACKGROUND OF THE INVENTION

Drug resistance has been an ever-lasting obstacle in treatment of refractory rheumatoid arthritis (refractory RA). Resistance to classical therapeutic agents could be classified into two major categories: intrinsic resistance that is genetically caused, and acquired resistance that develops as consequence of selective pressure under drug exposure. In fact, intrinsic drug resistance is more frequently found in inflammatory diseases, e.g. rheumatoid arthritis (RA). For instance, rheumatoid arthritis synovial fibroblasts (RASFs) exhibit apoptosis-resistance which is due to low level expression of TNF-related apoptosis-inducing ligand (TRAIL) death receptors. Such an apoptosis-resistant phenotype is considered as a major characteristic of the refractory cases of RA. RASFs also exhibits "tumor-like" phenotype, these cells have been re-conceptualized from passive structural cells to invasive, destructive, immunogenic, hyperplastic cells exhibiting multipotent inflammatory properties which contribute to the pathology of RA. The synovial environment in RA favours survival of RASFs and discourages their removal through apoptosis.

Apart from apoptotic proteins, the tumor suppressor p53 is a sensor of cellular stress and also a critical initiator of apoptosis. Generally, the high frequency of p53 mutations eventually leads to chemo-resistance of cancer cells. Surprisingly, somatic mutations of p53 are frequently identified in synovia of patients suffering from RA. In particular, dominant-negative p53 mutation of N239S and R213* contributes to apoptosis inhibition and inflammatory cytokine production. These findings suggest that p53 mutations may be involved in the mechanism of developing refractory RA.

Furthermore, patients suffering from refractory RA may exhibit multidrug resistance (MDR). Such a multidrug resistance may be intrinsic or acquired resistance. The MDR phenotype confers unresponsiveness to many diverse dugs by drug efflux, which may be mediated by ABC transporter protein. ABC transporter proteins have been found to be constitutively expressed and overexpressed, respectively, in many multidrug-resistant disease, wherein P-glycoprotein is considered for being a key player in the multidrug-resistant phenotype. P-glycoprotein (P-gp), a 170-kd ATP-dependent membrane transporter, which reduces intracellular drug concentrations to sub-optimal levels. Maillefert J F et al., Br J Rheumatol 1996 (35), reported that the percentage of peripheral blood lymphocytes expressing P-gp was significantly higher in RA patients treated with prednisolone, these might cause efflux of corticosteroids and disease-modifying anti-rheumatic drugs (DMARDs) from lymphocytes, and eventually develop drug-resistance in patients with severe inflammatory condition.

Consequently, there is a strong need for methods and means allowing for an effective therapeutic treatment especially of refractory rheumatoid arthritis and multidrug-resistant rheumatoid arthritis synovial fibroblasts, respectively. In particular, efficacious treatment options are urgently required for specifically treating subjects with refractory rheumatoid arthritis with expression or overexpression of ABC transporter proteins or decreased expression of pro-apoptotic proteins and increased expression of anti-apoptotic proteins, respectively, i.e. for treating said specific subgroups of subjects among subjects with rheumatoid arthritis.

SUMMARY OF THE INVENTION

The present invention relates in a first aspect to a method of treating a subject suffering from refractory rheumatoid arthritis, in particular at least one of (i) ABC-protein dependent refractory rheumatoid arthritis or (ii) an apoptosis-deficient refractory rheumatoid arthritis. The method of treating the subject with refractory rheumatoid arthritis comprises the step of administering an effective amount of a quinonemethide triterpenoid to said subject.

The quinonemethide triterpenoid administered according to the present invention has a structure of Formula (I) including any salt, solvate or anhydrate thereof:

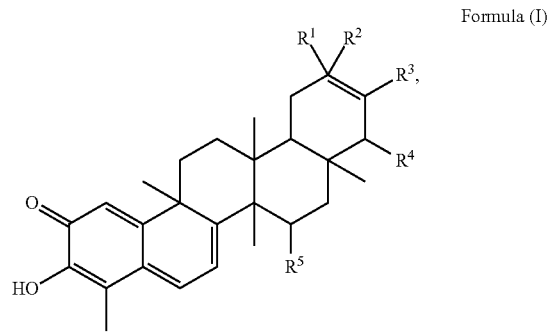

Formula (I)

wherein

═══ represents a single or double bond.

$R^1$ is selected from —$CH_3$, —$CH_2OH$, —OH or —H;

$R^2$ is selected from —$CH_3$, —$CH_2OH$, —OH, —COOH, —$COOCH_3$, =$CH_2$ or —H;

$R^3$ is selected from —OH, =O or —H;

$R^4$ is selected from —OH or —H;

$R^5$ is selected from —OH or —H.

In particular, the quinonemethide triterpenoid of the present invention has a structure of Formula (II):

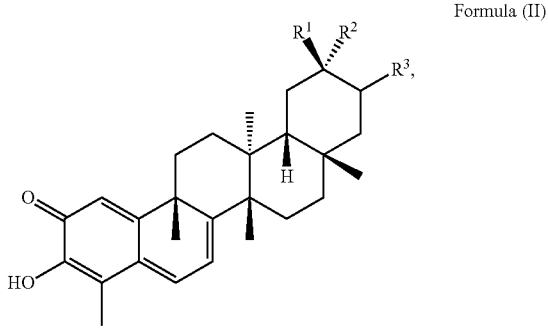

Formula (II)

wherein
R¹ is selected from —CH₃, or —CH₂OH;
R² is selected from —COOH or —COOCH₃;
R³ is selected from —OH, =O or —H.

More preferably, the quinonemethide triterpenoid of the present invention has a structure of Formula (IIIa):

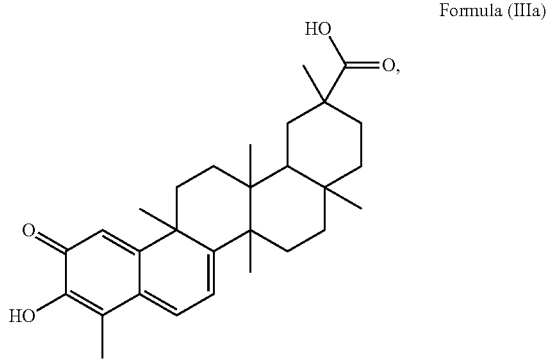 [SMILES: CC1=C(O)C(=O)C=C2C1=CC=C1C2(C)CCC2(C)C3CC(C)(C(=O)O)CCC3(C)CCC12C]

Formula (IIIa)

in particular a structure of Formula (IIIb):

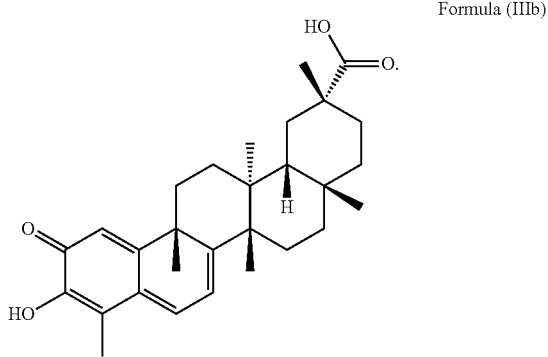

Formula (IIIb)

The compound of Formula (I) is in particular administered in combination with at least one further therapeutic compound used for treating rheumatoid arthritis such as an anti-arthritis compound selected from the group consisting of methotrexate, dexamethasone, prednisolone, abatacept, adalimumab, chloroquinem etanercept, golimumab, infliximab, leflunomide, rituximab, sulfasalazine, colchicine, or a derivative thereof.

According to the invention is also the quinonemethide triterpenoid described above for use as a medicament for the treatment of refractory rheumatoid arthritis, in particular ABC-protein-dependent such as P-glycoprotein-dependent refractory rheumatoid arthritis or apoptosis-deficient refractory rheumatoid arthritis associated with at least one of p53-mutation, or TRAIL death receptor-deficiency.

Another aspect of the invention pertains to the use of the quinonemethide triterpenoid described above in the preparation of a medicament for treating refractory rheumatoid arthritis, in particular ABC-protein-dependent such as P-glycoprotein-dependent or apoptosis-deficient associated at least one of p53-mutation, or TRAIL death receptor-deficiency. The quinonemethide triterpenoid described above is in particular used in combination with further therapeutic compounds, preferably therapeutic compounds which are used for treating rheumatoid arthritis such as an anti-arthritis compound as described above.

The present invention also relates to the use of the quinonemethide triterpenoid as described above as P-glycoprotein inhibitor or calcium mobilizer for treating refractory rheumatoid arthritis.

In another aspect, the present invention pertains to a method of inducing autophagy in a synovial fibroblast, in particular multidrug-resistant rheumatoid arthritis synovial fibroblast, comprising the step of contacting at least a population of synovial fibroblasts with a quinonemethide triterpenoid as described above or a salt, solvate or anhydrate thereof. In particular, the cell death of the synovial fibroblasts is induced or the growth of synovial fibroblasts is suppressed.

In still another aspect, the present invention provides a method of inducing calcium mobilization in a synovial fibroblast, in particular multidrug-resistant rheumatoid arthritis synovial fibroblast, comprising contacting a population of synovial fibroblasts with the quinonemethide triterpenoid as described above. In an embodiment, the synovial fibroblast is P-glycoprotein dependent or apoptosis-deficient associated with a p53 mutation. Said method alters the calcium homeostasis in the synovial fibroblasts and may ultimately trigger the death of the synovial fibroblasts.

The present invention further pertains to a pharmaceutical composition comprising an effective dose of the quinonemethide triterpenoid as described above and an effective dose of at least a further anti-arthritic compound commonly used for treating rheumatoid arthritis, namely selected from the group consisting of methotrexate, dexamethasone, prednisolone, abatacept, adalimumab, chloroquinem etanercept, golimumab, infliximab, leflunomide, rituximab, sulfasalazine, colchicine, or a derivative thereof. The pharmaceutical composition may further comprise excipients, in particular pharmaceutically acceptable excipients, such as a carrier, salt, buffer, water, or a combination thereof.

Accordingly, the present invention provides a novel and highly advantageous way for treating refractory rheumatoid arthritis (refractory RA) from various origins including either (i) the administration of the quinonemethide triterpenoid as described above or (ii) of the quinonemethide triterpenoid as described above as an adjuvant agent in combination with other anti-arthritis compounds. It has been found that the quinonemethide triterpenoid as described above of (IIIa) or (IIIb) is especially suitable for inducing autophagy and inducing apoptosis in particular via promoting calcium mobilization so as to accumulate autophagosomes and reduce inflammation. The quinonemethide triterpenoid is also suitable for inhibiting ABC protein activity, in particular P-glycoprotein activity leading to an accumulation of cytotoxic compounds or therapeutic compounds in said synovial fibroblasts in particular multidrug-resistant RASFs while having exceptionally increased cytotoxic activity specifically towards RASFs. Said quinonemethide triterpenoid described above in particular allows for effectively targeting said refractory rheumatoid arthritis and RASFs, respectively, either alone or in combination with conventional anti-arthritis compounds. Therefore, the present invention provides an advantageous treatment exceptionally suitable to specifically address refractory RA.

DESCRIPTION OF THE EMBODIMENTS

Figure 1A:
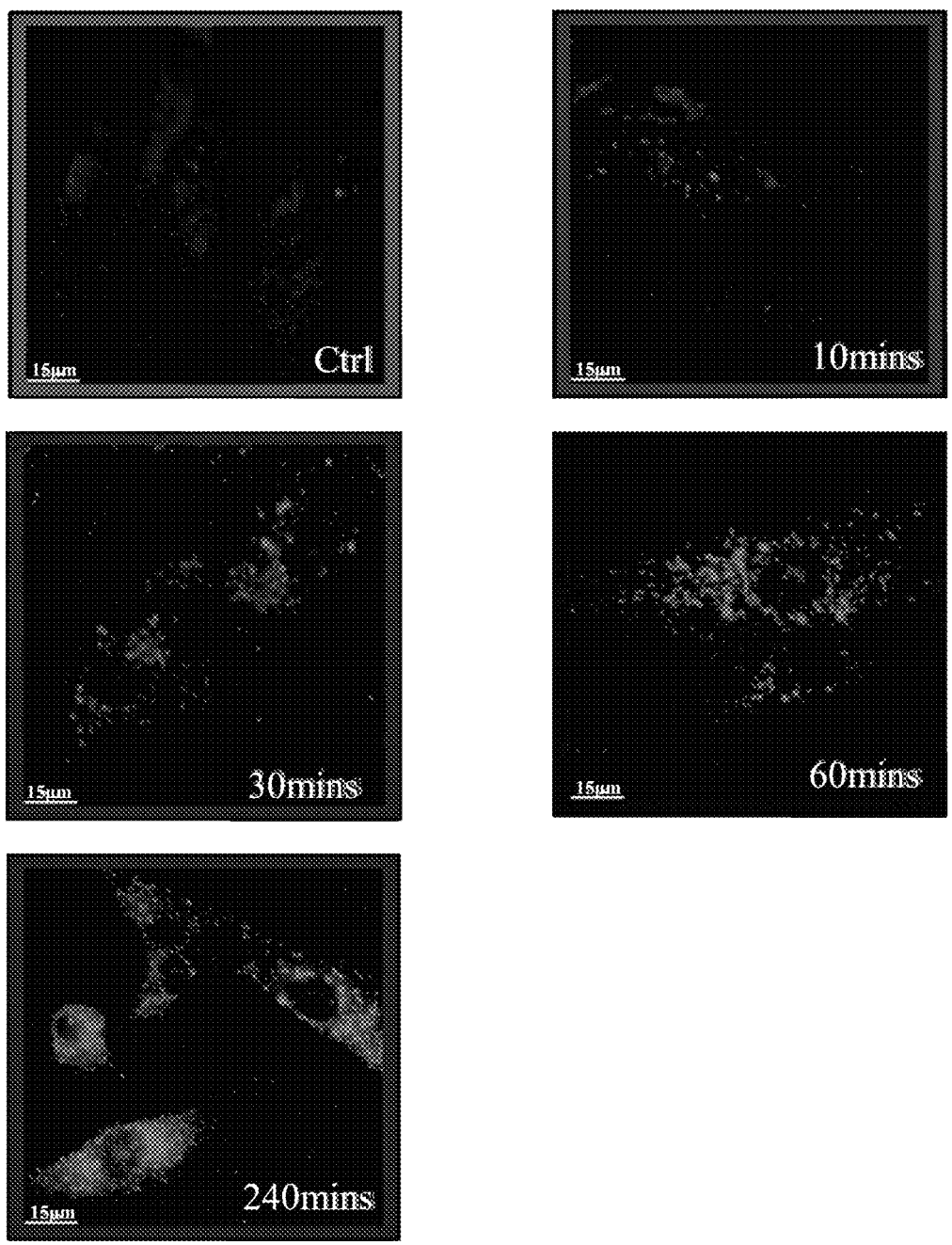
FIG. 1A shows images obtained from immunocytochemistry staining, which reflects the time-dependent effect of celastrol in induction of autophagy in rheumatoid arthritis synovial fibroblasts (RASFs). RASFs were treated with DMSO as a control group or 1 μM celastrol for 10, 30, 60 or 240 min. The cells were then fixed and visualized for endogenous LC3-II expression by fluorescence microscopy using LC3-II antibody plus TRITC-conjugated anti-mouse secondary antibody.

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

The present invention relates in a first aspect to a method of treating a subject suffering from refractory rheumatoid arthritis (refractory RA). Said method of treating refractory RA comprises the step of administering an effective amount of a quinonemethide triterpenoid to said subject. The quinonemethide triterpenoid can be a synthetic one or obtained from extracts of respective plants, in particular a quinonemethide triterpenoid obtained from plants of the family Celastraceae, in particular from plants of the genus *Celastrus, Catha, Maytenus, Salacia* and/or *Tripterygium*, more preferably from plants of the genus *Celastrus* and/or *Tripterygium*.

The term quinonemethide triterpenoid generally refers to a subclass of pentacyclic triterpenoids derived from the oleanane basic structure. The quinonemethide triterpenoid of the present invention has a structure of Formula (I) including any salt, solvate or anhydrate thereof:

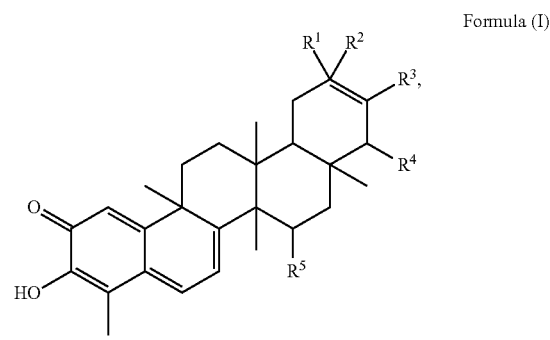

Formula (I)

wherein ═══ represents a single or double bond.

$R^1$ is selected from —CH$_3$, —CH$_2$OH, —OH or —H. Preferably, $R^1$ is selected from —CH$_3$ or —CH$_2$OH.

$R^2$ is selected from —CH$_3$, —CH$_2$OH, —OH, —COOH, —COOCH$_3$, ═CH$_2$ or —H. Preferably, $R^2$ is selected from —COOH or —COOCH$_3$.

$R^3$ is selected from —OH, ═O or —H.

$R^4$ is selected from —OH or —H.

$R^5$ is selected from —OH or —H.

Also contemplated by the present invention are any pharmaceutically acceptable salts, hydrates, solvates, anhydrates as well as enantiomers and their mixtures, stereoisomeric forms, racemates, diastereomers and their mixtures of the quinonemethide triterpenoid of the present invention.

As used herein, the term "solvate" refers to a complex of variable stoichiometry formed by a solute, i.e. the quinonemethide triterpenoid, and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition. The terms stereoisomers, diastereomers, enantiomers and racemates are known to the skilled person.

Preferably, the quinonemethide triterpenoid of the present invention has a structure of Formula (II):

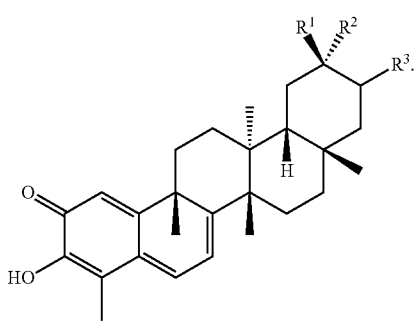

Formula (II)

$R^1$ is selected from —$CH_3$ or —$CH_2OH$, more preferably $R^1$ is —$CH_3$. $R^2$ is selected from —COOH or —$COOCH_3$, more preferably $R^2$ is —COOH. $R^3$ is selected from —OH, =O or —H, more preferably $R^3$ is —H.

In a preferred embodiment of the present invention, the quinonemethide triterpenoid of the present invention has the structure of Formula (IIIa):

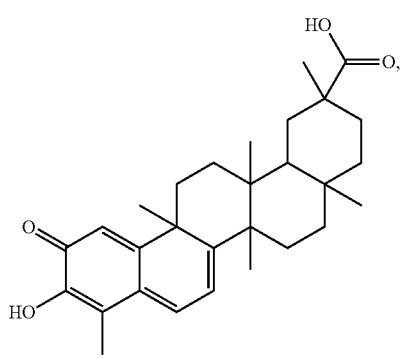

Formula (IIIa)

including any salt, solvate or anhydrate thereof and Including any stereoisomer, diastereomer, enantiomer or racemate thereof.

In particular, the quinonemethide triterpenoid has the structure of Formula (IIIb):

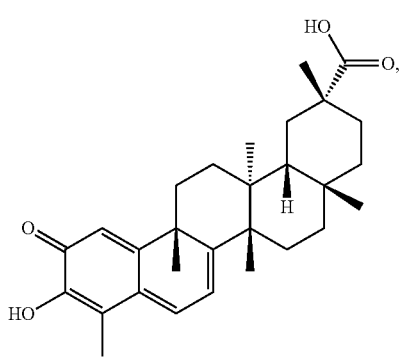

Formula (IIIb)

including any salt, solvate or anhydrate thereof. Said compound of Formula (IIIb) is known as celastrol and can be prepared according to methods known to the skilled person or isolated from *Tripterygium Wilfordii* (Thunder of God vine) and *Celastrus Regelii*.

The expression "effective amount" and "effective dose" generally denote an amount sufficient to produce therapeutically desirable results, wherein the exact nature of the result varies depending on the specific disorder which is treated. When the disorder is refractory RA, the result is usually an inhibition or suppression of the proliferation of synovial fibroblasts, a reduction of synovial fibroblasts or the amelioration of symptoms related to the refractory RA such as reduction of inflammation.

The subject can be a human or animal, in particular the subject is a mammal, preferably a human. The subject is, thus, preferably a human suffering from refractory RA. Said subject, thus, includes human subjects having a multidrug resistance to conventional therapeutic agents which induce cell death in synovial fibroblasts, i.e. which are used to treat refractory RA.

The effective amount of the quinonemethide triterpenoid of the present invention may depend on the species, body weight, age and individual conditions of the subject and can be determined by standard procedures such as with cell cultures or experimental animals. When the subject is a human, the effective amount is preferably about 0.1 mg/kg to about 0.5 mg/kg, 0.13 mg/kg to about 0.3 mg/kg, 0.135 mg/kg, or 0.27 mg/kg. In an embodiment where the subject is a rodent, the effective amount is preferably about 0.5 mg/kg to 3 mg/kg, 1 mg/kg to 2 mg/kg, 1 mg/kg, or 2 mg/kg. The quinonemethide triterpenoid is preferably administered for at least 1 day, at least 2 days, at least 5 day or at least 10 days depending on the severity of the illness.

The term "rheumatoid arthritis" (RA) refers to an autoimmune disease that primarily causes chronic inflammation at joints, and in some cases at other body parts. The subject suffering from RA typically has swollen and painful joints, feels stiffness and loss of function in joints. The term "refractory" refers to a specific type of RA where the subject does not show sufficient or even no therapeutic response toward an anti-arthritis drug conventionally used. I.e. the subject suffering from refractory RA shows multidrug-resistance toward one or more conventional therapeutic agents used in the treatment of RA. Such a multidrug-resistance may be intrinsic or acquired. The acquired resistance may be developed due to inappropriate or delayed treatment or overexposure to conventional therapeutic agents. In general, the subject suffering from refractory RA has multidrug-resistant rheumatoid arthritis synovial fibroblasts and has a resistant factor toward a conventional therapeutic agent of at least 1.4 or above.

The method provided herein is used and particularly effective in treating subjects suffering from refractory RA, in particular suffering from at least one of ABC-protein dependent refractory RA or apoptosis-deficient refractory RA.

ABC-protein dependent refractory RA, i.e. mediated by ABC transporter proteins (hereinafter "ABC-proteins") such as by P-glycoprotein, i.e. is associated with an enhanced expression or enhanced functional activity of at least one ABC-protein in the rheumatoid arthritis synovial fibroblasts (RASFs), in particular of P-glycoprotein.

Apoptosis-deficient refractory RA, i.e. associated with a decreased expression of at least one pro-apoptotic protein and/or decreased pro-apoptotic activity of at least one pro-apoptotic protein and/or enhanced expression of at least one anti-apoptotic protein and/or enhanced anti-apoptotic activity of at least one anti-apoptotic protein in the RASFs; in particular the RASFs harbors a p53 mutant.

In one embodiment, the refractory RA is ABC-protein dependent and in particular P-glycoprotein (P-gp) dependent. In another embodiment of the present invention, the refractory RA is apoptosis-deficient, in particular associated with a p53 mutation, i.e. harboring a p53 mutant and/or associated with a deficiency in TRAIL death receptor.

ABC-proteins are transporter proteins that may act to remove therapeutic agents from cells. The, thus, resulting multidrug-resistant phenotype can be specifically detected in a subject, tissue, or cell by administering to the subject, tissue, or cell, a compound such as an anti-arthritis compound which is transported by the ABC-proteins, i.e. is a substrate to ABC-proteins such as to P-glycoprotein. The method then encompasses determining the amount of said anti-arthritis compound in the cells compared with the amount in a reference control, i.e. cells that do not express said multidrug-resistance phenotype.

Said ABC-protein is in particular selected from the "B" subfamily, "C" subfamily or "G" subfamily of ABC-proteins. Preferably, the ABC-protein is the protein encoded by ABCB1, ABCB4, ABCB5 or ABCB11 in humans or corresponding genes in other mammals which can transport drugs, in particular ABCB1 and/or ABCB5. In an embodiment of the present invention, said ABC-protein is P-glycoprotein, the refractory RA is a P-glycoprotein-dependent refractory RA. P-glycoprotein as used herein refers to the protein as encoded by the ABCB1 and/or ABCB5 gene in humans or respective genes including SNPs and naturally occurring mutations to said gene and as encoded by corresponding genes in other mammals, respectively.

An enhanced expression and/or enhanced functional activity of at least one ABC-protein, i.e. ABC-protein-dependent refractory RA, means an expression and/or functional activity exceeding, in particular significantly exceeding, the one in normal cells or tissue, i.e. synovial fibroblasts without the multidrug-resistant phenotype. The term "enhanced expression" or "enhanced functional activity" of at least one ABC-protein such as P-glycoprotein includes embodiments in which the multidrug-resistant rheumatoid arthritis synovial fibroblasts express the ABC-protein such as P-glycoprotein, whereas in the reference control, i.e. synovial fibroblasts without the multidrug-resistant phenotype, said ABC-protein such as P-glycoprotein is not expressed, at all. I.e. when said reference control does not express the ABC-protein such as P-glycoprotein, multidrug-resistant rheumatoid arthritis synovial fibroblasts having a detectable expression or functional activity of the ABC-protein such as P-glycoprotein are ABC-protein-dependent such as P-glycoprotein-dependent by definition.

Whether the refractory RA is ABC-protein-dependent such as P-glycoprotein-dependent can be determined by methods known to the skilled person in particular comprising immunological methods accompanied by the use of MDR-specific antibodies, immunocytochemistry and immunohistochemistry, respectively, by determining respective mRNA levels such as with Northern blots or quantitative RT-PCR, with MDR-specific antibodies in vivo or with an ABC-protein such as P-glycoprotein efflux assay detecting the efflux of a marker.

In particular, an ABC-protein such as P-glycoprotein efflux assay can be used for determining the functional activity of ABC-proteins, i.e. for determining whether the refractory RA is ABC-protein-dependent. Markers which can be used in said efflux assay include drugs which are a substrate for the respective ABC-protein, a radionuclide or a dye like a fluorescent dye selected from Rhodamine123 (also referenced as "Rho123", 6-amino-9-(2-methoxycarbonylphenyl) xanthen-3-ylidene]azanium chloride), DiOC2 (3,3'-diethyloxacarbocyanine iodide) or Calcein AM (calcein o,o'-diacetate tetrakis(acetoxymethyl)ester). The cells to be analyzed are usually incubated with the marker at physiological conditions, i.e. in particular at about 37° C. for at least 20 min, in particular for at least 30 min and especially for about 1 h. Usually, the cells are washed subsequently at least 1-time, in particular more than 1-time preferably with a buffer, in particular 5-times with ice-cold Phosphate-buffered saline (PBS). Elimination from or, alternatively, retention of the marker in the multidrug-resistant cells can be determined and compared with a reference control, i.e. cells with ABC-protein expression as present in cells that do not have a multidrug-resistance phenotype of the same cell or tissue type. For example, fluorescence of a fluorescent marker can be determined by flow cytometry.

Preferably, an ABC-protein-dependent such as a P-glycoprotein-dependent refractory RA comprises synovial fibroblasts in particular multidrug-resistant RASFs with an expression of ABC-protein or ABC-protein functional activity exceeding the one in the reference control by at least 5%, in particular by at least 10%. For example, the expression or functional activity of P-glycoprotein in P-glycoprotein-dependent synovial fibroblasts is at least 5% or at least 10% higher than the expression or functional activity of P-glycoprotein in the reference control.

The term "apoptosis-deficient" used herein refers to a refractory RA having at least one of (i) decreased expression and/or decreased pro-apoptotic activity of at least one pro-apoptotic protein or (ii) enhanced expression and/or enhanced anti-apoptotic activity of at least one anti-apoptotic protein or both of them, i.e. (i) and (ii). Pro- and/or anti-apoptotic proteins in particular include p53 mutant, Bcl-2 proteins, PARP, apoptosis proteins and TRAF receptor proteins.

Whether a refractory RA is apoptosis-deficient can be determined by methods known to the skilled person, namely by measuring the expression of the pro-apoptotic protein and/or anti-apoptotic protein and/or by determining the apoptotic activity of the pro-apoptotic protein and/or the anti-apoptotic protein compared with a reference control, namely synovial fibroblasts that do not have a multidrug-resistance phenotype. Suitable methods for determining the expression may include immunological methods accompanied by the use of specific antibodies, immunocytochemistry and immunohistochemistry, respectively, or by determining respective mRNA levels such as with Northern blots or quantitative RT-PCR. The apoptotic activity can be determined by assays which determine the rate of apoptosis known to the skilled person such as assays determining cytomorphological alterations, DNA fragmentation such as by TUNEL assay and flow cytometry, detection of apoptosis pathway downstream targets, cleaved substrates, regulators and inhibitors, membrane alterations, or mitochondrial assays. As one of skill in the art will appreciate, any suitable means of detecting apoptosis may be used in the method of the invention.

Anti-apoptotic proteins are proteins which prevent cell apoptosis. The at least one anti-apoptotic protein is preferably selected from the Bcl-2-family. Enhanced expression and/or enhanced anti-apoptotic activity of the anti-apoptotic protein in particular means an expression and/or anti-apoptotic activity of said at least one protein which is increased by at least 5%, more preferably at least 10% and most preferably by more than 50% compared with a reference control, namely synovial fibroblasts without the multidrug-resistant phenotype. Enhanced expression and/or enhanced anti-apoptotic activity of the anti-apoptotic protein may be caused, for example, by an increased expression of anti-apoptotic wild-type protein or and/or an expression of an anti-apoptotic mutant protein having increased anti-apoptotic activity. A mutant anti-apoptotic protein has an amino acid sequence different from the wild-type protein expressed in healthy cells without a mutation in the respective encoding genes.

Pro-apoptotic proteins are proteins which induce and in particular initiate the cell apoptosis pathway. In particular, pro-apoptotic proteins are selected from at least one of p53 protein and pro-apoptotic proteins of the Bcl2-family. The term "p53 protein" used herein includes respective p53 isoforms encoded by the TP53 gene such as p53α, p53β, p53γ, Δ40p53α, Δ40p53β, Δ40p53γ, Δ133p53α, Δ133p53β, Δ133p53γ, Δ160p53α, Δ160p53β, Δ160p53γ and the like. Pro-apoptotic proteins of the Bcl-2-family are preferably selected from at least one of Bax, Bak, Bad, Bik, Bim, PUMA, NOXA, Bok, Bad, Bmf, Hrk and Bid, in particular of at least one of Bax or Bak. Decreased expression and/or decreased pro-apoptotic activity of pro-apoptotic proteins in particular means an expression and/or pro-apoptotic activity of said at least one protein which is decreased by at least 5%, more preferably by at least 10% and most preferably by more than 50% compared with a reference control, namely synovial fibroblasts without the multidrug-resistant phenotype. Decreased expression and/or decreased pro-apoptotic activity of at least one pro-apoptotic protein may be caused by, for example, a decreased expression of pro-apoptotic wild-type protein and/or by an expression of a pro-apoptotic mutant protein with decreased pro-apoptotic activity. A mutant pro-apoptotic protein has an amino acid sequence different from the wild-type protein expressed in healthy cells without a mutation in the respective encoding genes.

Most preferably, the apoptosis-deficient refractory RA exhibits a decreased expression or decreased pro-apoptotic activity of at least one pro-apoptotic protein. In particular, the subject or cells having apoptosis-deficient refractory RA harbor a p53 mutant.

The quinonemethide triterpenoid is in preferred embodiments of the present invention administered in combination with an effective amount of at least one anti-arthritis compound. As used herein, the term "anti-arthritis compound" includes drugs which are advantageously and commonly administered to a subject or cells without the multidrug resistance phenotype, i.e. which have been known to be used in the treatment of RA.

In particular, the anti-arthritis compound is selected from the group consisting of the group consisting of methotrexate, dexamethasone, prednisolone, abatacept, adalimumab, chloroquinem etanercept, golimumab, infliximab, leflunomide, rituximab, sulfasalazine, colchicine, or a derivative thereof. Preferably, the chemotherapeutic compound is selected from the group consisting of methotrexate, dexamethasone or prednisolone.

In especially preferred embodiments of the present invention, the quinonemethide triterpenoid has the structure of Formula (IIIa) or (IIIb):

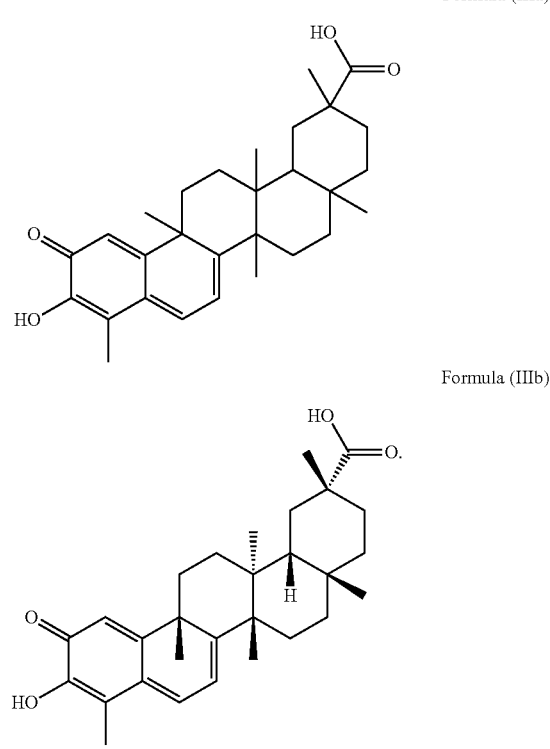

Formula (IIIa)

Formula (IIIb)

The anti-arthritis compound can be administered before, after or simultaneously with the quinonemethide triterpenoid, in particular before or simultaneously with the quinonemethide triterpenoid, further preferred simultaneously with the quinonemethide triterpenoid.

The method of the present invention may comprise further steps before administering the compound of Formula (I), in particular the quinonemethide triterpenoid of Formula (II), (IIIa) or (IIIb) of
  obtaining a sample, in particular synovial fibroblasts, from the subject;
  testing said sample for at least one of
    the expression of at least one ABC-protein, in particular of P-glycoprotein;
    the at least one ABC-protein, in particular the P-glycoprotein, functional activity;
    the expression of at least one pro- or anti-apoptotic protein, in particular selected from at least one of p53, Bax or Bak;
    the pro-apoptotic activity of at least one pro- or anti-apoptotic protein, in particular selected from at least one of p53, Bax or Bak;
  optionally correlating the expression and/or functional activity of the at least one ABC-protein, in particular of P-glycoprotein, and/or the expression or activity of the at least one pro- or anti-apoptotic protein with an outcome and if conditions are met, administrating the quinonemethide triterpenoid, in particular the quinonemethide triterpenoid of Formula (II), (IIIa) or (IIIb), to said subject; alone or in combination with a chemotherapeutic compound.

The skilled person is aware of methods for determining the expression of P-glycoprotein such as an antibody assay or its functional activity such as with an efflux assay for example by incubating the cells with a dye such as Rhodamine123 as well as of methods for determining the expression or activity of pro- or anti-apoptotic proteins.

According to the invention is also the compound of Formula (I), in particular of Formula (II), (IIIa) or (IIIb), for use as a medicament for the treatment of refractory RA, in particular P-glycoprotein dependent refractory RA or apoptosis-deficient refractory RA. The compound of Formula (I), in particular of Formula (II), (IIIa) or (IIIb), can be used in an effective amount for treating an animal or a human, in particular mammal, preferably a human.

Another aspect of the invention refers to the use of the compound of Formula (I), in particular of Formula (II), (IIIa) or (IIIb), for preparing a medicament for treating refractory RA, in particular P-glycoprotein dependent refractory RA and/or apoptosis-deficient refractory RA. In particular, the apoptosis-deficient refractory RA is associated with a p53 mutation. The compound of Formula (I), in particular of Formula (II), (IIIa) or (IIIb), may be used in combination with at least a further therapeutic compound, preferably therapeutic compounds which are used for treating RA such as an anti-arthritis compound.

The present invention also relates to a method of using compound of Formula (I), in particular of Formula (II), (IIIa) or (IIIb), as P-glycoprotein efflux pump inhibitor or calcium mobilizer for treating refractory RA comprising applying an effective amount of said compound for inhibiting P-glycoprotein or promoting calcium mobilization in synovial fibroblasts in particular in multidrug-resistant RASFs, thereby triggering cell death and relieving the associated symptoms.

In another aspect of the present invention, the invention provides a method for inducing autophagy in a synovial fibroblast, in particular multidrug-resistant rheumatoid arthritis synovial fibroblast (RASFs), comprising the step of contacting at least a population of synovial fibroblasts with a quinonemethide triterpenoid as described above or a salt, solvate or anhydrate thereof. In particular, the cell death of the synovial fibroblasts is induced or the growth of synovial fibroblasts is suppressed. MTT assay or flow cytometry analysis may be used for measuring the effect on cell death and cell viability.

The synovial fibroblasts are in particular ABC-protein-dependent, most preferably P-glycoprotein-dependent and/or apoptosis-deficient as described above. In one embodiment of the present invention, the synovial fibroblast is rheumatoid arthritis synovial fibroblast and in particular harbors a p53 mutant.

In embodiments of the present invention, the synovial fibroblasts are resistant against an anti-arthritis compound as described above or have a resistant factor toward the conventional therapeutic agent of at least 1.2.

The concentration of the quinonemethide triterpenoid used for contacting the synovial fibroblasts may range from 0.1 µM to 5 µM, preferably from 0.1 µM to 2 µM, in particular 0.25 µM, 0.5 µM, 0.75 µM, 1 µM, 1.25 µM, 1.5 µM or 2 µM. The synovial fibroblasts are preferably contacted with the quinonemethide triterpenoid of the present invention for at least 10 min, at least 15 min, at least 30 min, or at least 60 min.

Preferably, the $IC_{50}$ of the quinonemethide triterpenoid towards the multidrug-resistant RASFs is at most 5 µM, more preferably at most 2 µM or in particular about 1 µM. In an embodiment, the $IC_{50}$ is about 1 µM after about 72 h. The Resistant Factor of the quinonemethide triterpenoid of the present invention towards the multidrug-resistant RASFs is preferably less than 1.5 or about 1±0.5. The Resistant Factor is calculated by dividing the $IC_{50}$ of the quinonemethide triterpenoid towards multidrug-resistant RASFs showing resistant to conventional therapeutic agents by its $IC_{50}$ towards synovial fibroblasts which do not have a multidrug-resistant phenotype. A Resistant Factor<1 indicates that a compound is especially effective in treating refractory RA or inducing apoptosis and/or autophagy in ABC-dependent or apoptosis-deficient synovial fibroblasts.

In especially preferred embodiments of the present invention, the quinonemethide triterpenoid used for contacting the synovial fibroblast has the structure of Formula (IIIa) or (IIIb):

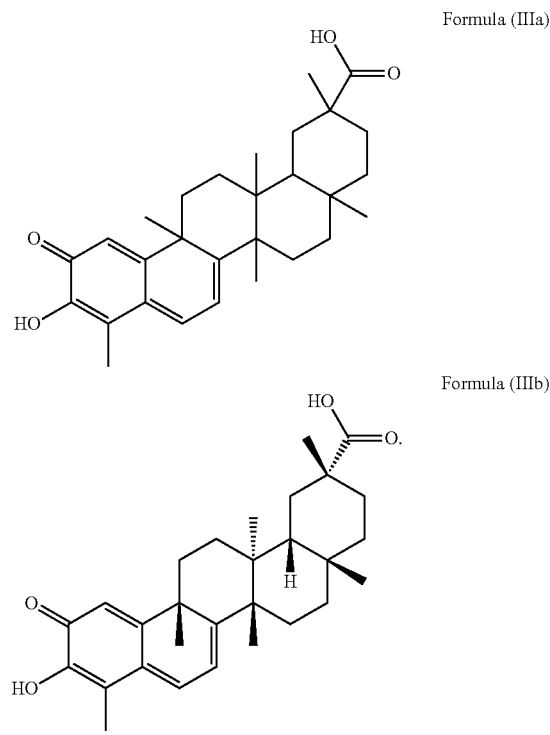

and the synovial fibroblast is contacted with between 0.1 µM and 2 µM of said quinonemethide triterpenoid.

The step of contacting the synovial fibroblast with the quinonemethide triterpenoid of the present invention, in particular of Formula (II), (IIIa) or (IIIb), may be carried out by applying an incubation solution comprising the compound of Formula (I), (II), (IIIa) or (IIIb) to said synovial fibroblast which incubation solution may further comprise suitable excipients such as buffers or a suitable growth medium.

The method may further comprise contacting said cells with a further therapeutic compound, in particular an anti-arthritis compound selected from the group consisting of methotrexate, dexamethasone, prednisolone, abatacept, adalimumab, chloroquinem etanercept, golimumab, infliximab, leflunomide, rituximab, sulfasalazine, colchicine, or a derivative thereof; before, at the same time with or subsequent to the application of the quinonemethide triterpenoid of the present invention. Preferably, the growth of the multidrug-resistant RASFs is suppressed and/or cell death is induced.

In a further aspect, the present invention refers to a method of inducing calcium mobilization in a synovial fibroblast, in particular multidrug-resistant RASFs, comprising contacting a population of synovial fibroblasts with a quinonemethide triterpenoid as described above or a salt, solvate or anhydrate thereof.

The synovial fibroblast is as described above, in particular the synovial fibroblast is multidrug-resistant rheumatoid arthritis synovial fibroblast (RASFs). In an embodiment, the synovial fibroblast is at least ABC-protein dependent, or apoptosis-deficient. Preferably, the synovial fibroblast is P-glycoprotein dependent having an overexpression of P-gp. In another embodiment, the synovial fibroblast is apoptosis-deficient which harbors a p53 mutant and has an overexpression of an anti-apoptotic protein and/or decreased expression of a pro-apoptotic protein.

The quinonemethide triterpenoid is found to be effective on affecting the calcium homeostasis in the synovial fibroblasts. In particular, the quinonemethide triterpenoid increases the free cytosolic calcium level in RASFs via inhibition of sarco/endoplasmic reticulum $Ca^{2+}$-ATPase (SERCA). Accordingly, the quinonemethide triterpenoid further promotes the cell death of RASFs.

The concentration of the quinonemethide triterpenoid used for contacting the synovial fibroblasts may range from 0.1 μM to 2 μM, in particular 0.1 μM, 0.2 μM, 0.5 μM, 1 μM or 2 μM. The synovial fibroblasts are preferably contacted with the quinonemethide triterpenoid of the present invention for at least 10 min, at least 15 min, at least 30 min, or at least 60 min.

Preferably, the synovial fibroblasts are contacted with a quinonemethide triterpenoid having a structure of Formula (IIIa) or (IIIb):

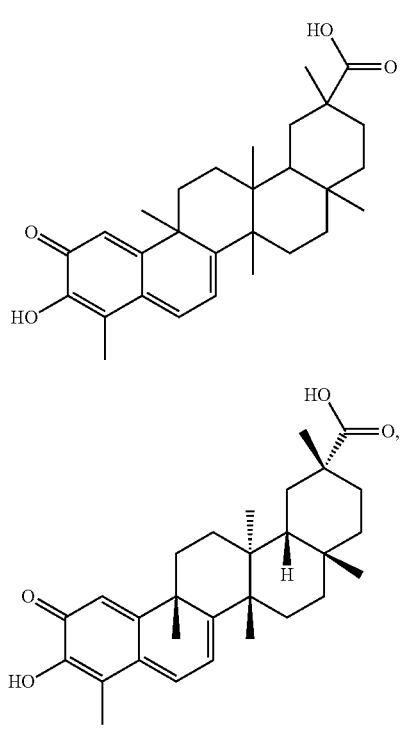

Formula (IIIa)

Formula (IIIb)

wherein the synovial fibroblast is preferably contacted with between 1 μM and 2 μM of the quinonemethide triterpenoid.

Further, the present invention pertains to a pharmaceutical composition comprising an effective dose of
(i) a quinonemethide triterpenoid as described above;
(ii) at least one chemotherapeutic compound selected from the group consisting of methotrexate, dexamethasone, prednisolone, abatacept, adalimumab, chloroquinem etanercept, golimumab, infliximab, leflunomide, rituximab, sulfasalazine, colchicine, or a derivative thereof, more preferably selected from the group consisting of methotrexate, decamethasone, prednisolone, or a derivative thereof.

The pharmaceutical composition may further comprise excipients, in particular pharmaceutically acceptable excipients, such as a carrier, salt, buffer, water, or a combination thereof. The skilled person is able to select suitable excipients.

The quinonemethide triterpenoid according to the invention can be present in solid, semisolid or liquid form to be administered by an oral, rectal, topical, parenteral or transdermal or inhalative route to a subject, preferably a human.

Preferably, the quinonemethide triterpenoid has a structure of Formula (IIIa) or (IIIb):

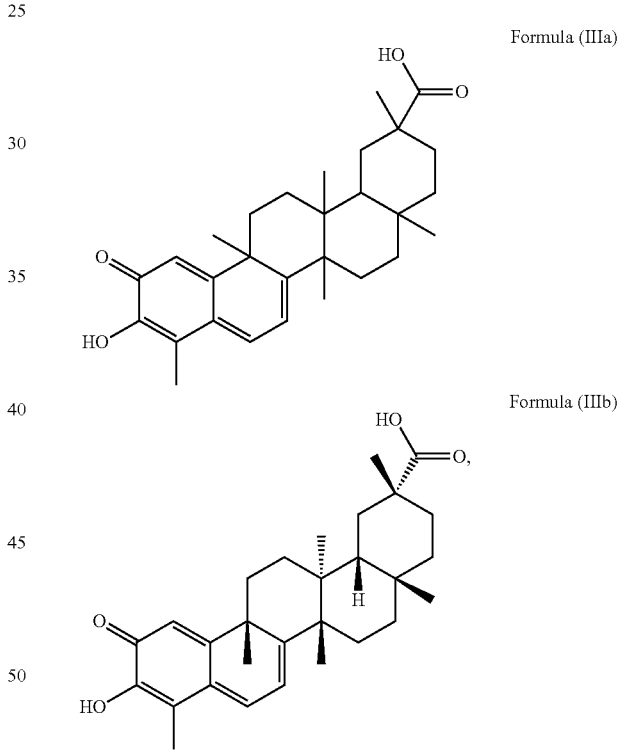

Formula (IIIa)

Formula (IIIb)

and the anti-arthritis compound is methotrexate, dexamethasone, prednisolone, or a derivative thereof.

EXAMPLES

Example 1

Autophagy Induction in RASFs and RAFLS

In the examples, both rheumatoid arthritis synovial fibroblasts (RASFs) isolated from RA patients and rheumatoid arthritis fibroblast-like synoviocytes (RAFLS) derived from the RASFs were used.

In order to determine endogenous expression of LC3-II, RASFs or RAFLS treated with indicated time and concentrations of celastrol (Cel) were fixed and visualised by fluorescence microscopy after staining with an LC3-II antibody followed by TRITC-conjugated anti-mouse secondary antibody.

Annexin V flow cytometry analysis was applied. Cell death and viability are measured using an Annexin V staining kit (BD Biosciences, San Jose, Calif., USA). Briefly, RAFLS are treated with 0-2 µM celastrol for 24 h. Cells are then harvested and analysed by multiparametric flow cytometry using FITC-Annexin V and Propidium iodide staining (BD Biosciences, San Jose, Calif., USA) according to the manufacturer's instructions. Flow cytometry is then carried out using a FACSCalibur flow cytometer (BD Biosciences, San Jose, Calif., USA). Data acquisition and analysis is performed with CellQuest (BD Biosciences, San Jose, Calif., USA). Data are obtained from three independent experiments.

Figure 1B:
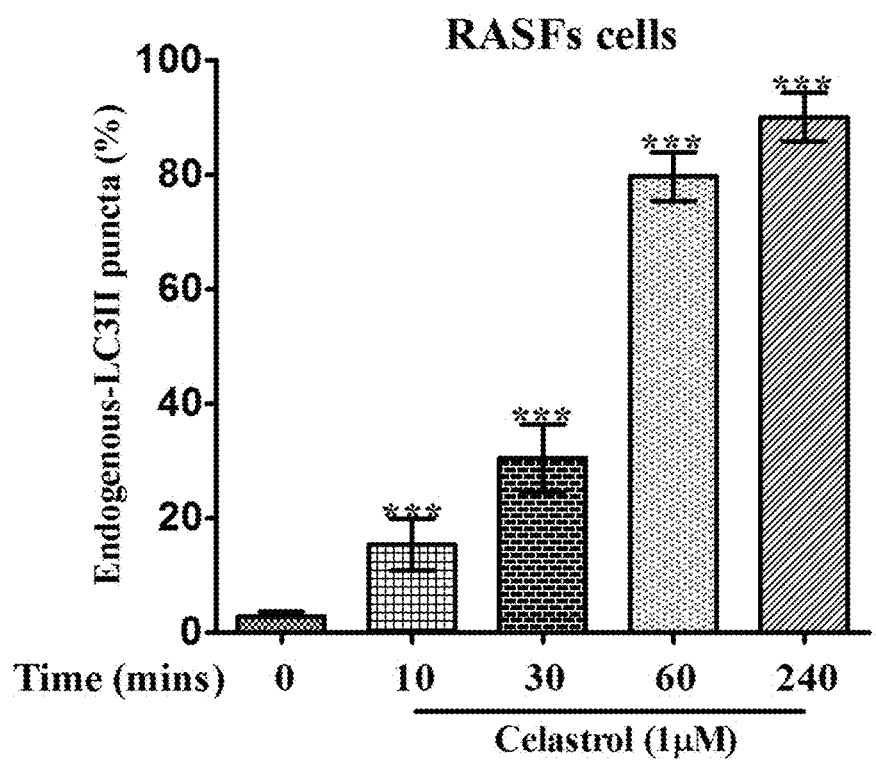
FIG. 1B shows the percentage of RASFs expressing endogenous LC3-II puncta after treatment of 1 μM celastrol for 10, 30, 60 or 240 min and treatment of DMSO as the control group. Data from the bar chart represented the mean values±S.D. of three independent experiments; error bars, S.D. ***, P<0.001.
Figure 2A:
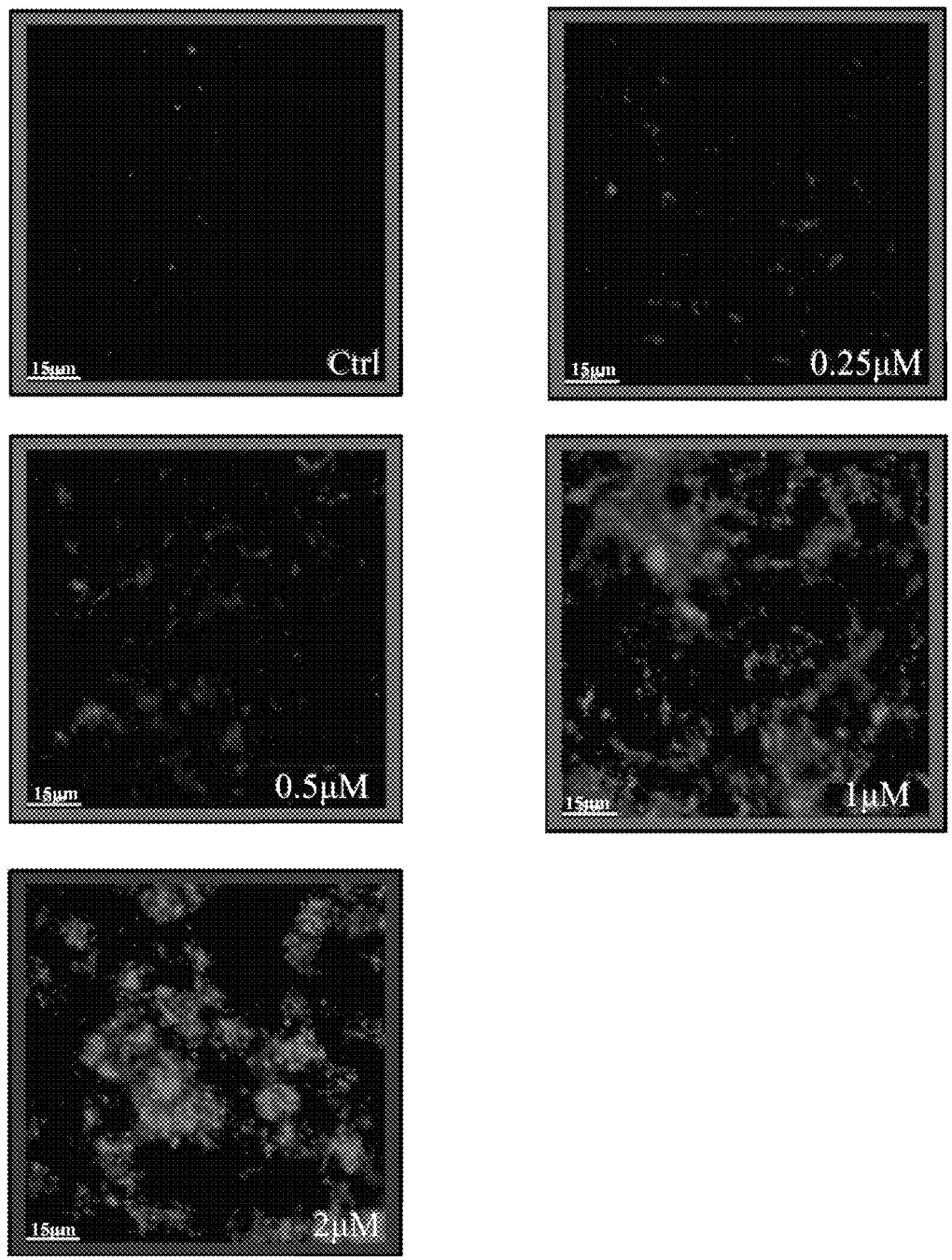
FIG. 2A shows images obtained from immunocytochemistry staining, which demonstrates the effects of celastrol on autophagy induction in rheumatoid arthritis fibroblast-like synoviocytes (RAFLS). RAFLS were treated with DMSO as a control group or celastrol at a concentration of 0.25, 0.5, 1 or 2 μM for 24 h. The results demonstrate that celastrol exerts a dose-dependent autophagy induction in RAFLS.
Figure 2B:
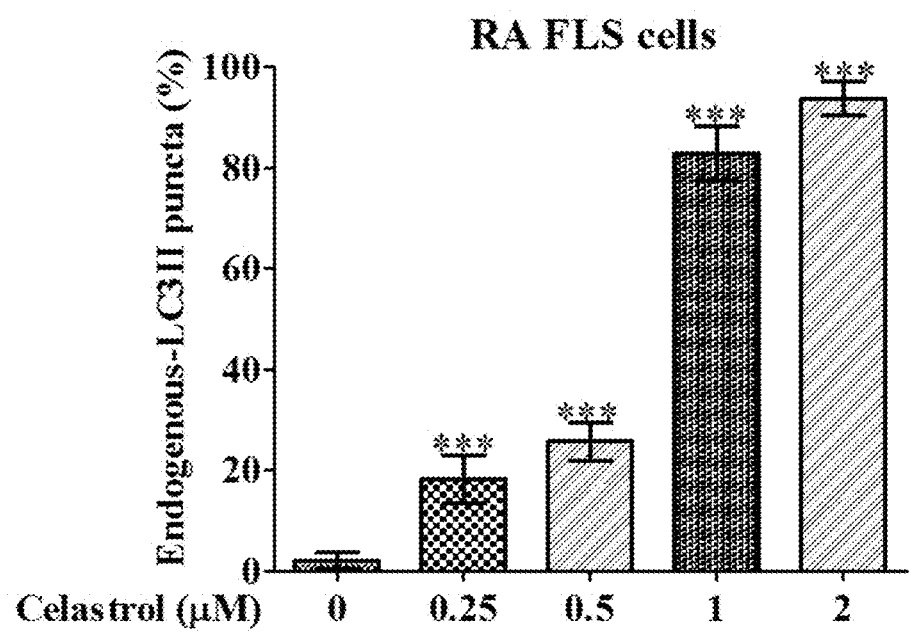
FIG. 2B shows the percentage of RAFLS expressing endogenous LC3-II puncta after treatment of 0, 0.25, 0.5, 1 or 2 μM celastrol for 24 h. Data from the bar chart represented the mean values±S.D. of three independent experiments; error bars, S.D. ***, P<0.001.
Figure 3A:
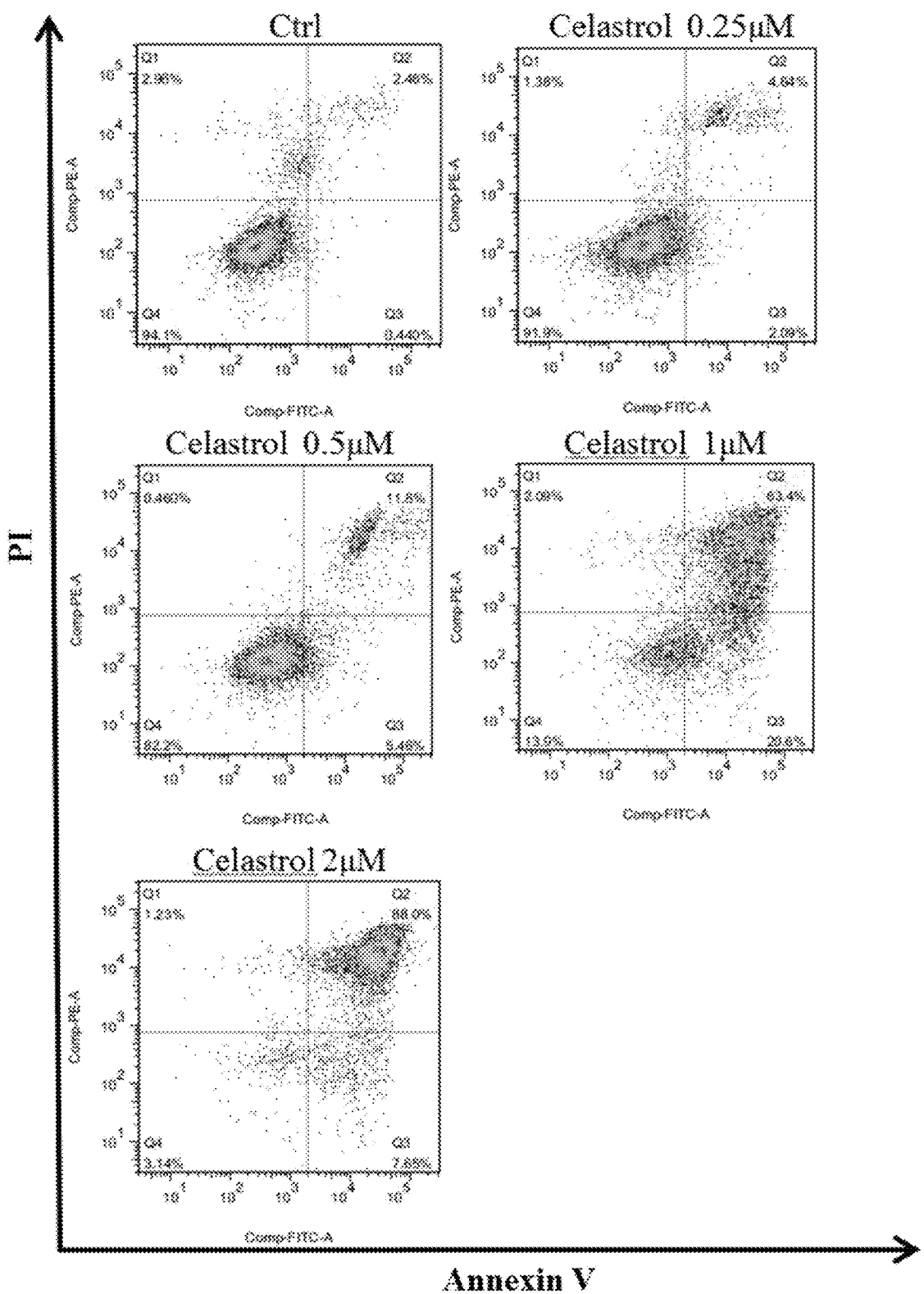
FIG. 3A shows the results obtained from flow cytometry analysis of RAFLS treated with DMSO as the control group and RAFLS treated with 0.25, 0.5, 1 or 2 μM celastrol for 24 h. The results demonstrate that celastrol has dose-dependent cytotoxicity against RAFLS.
Figure 3B:
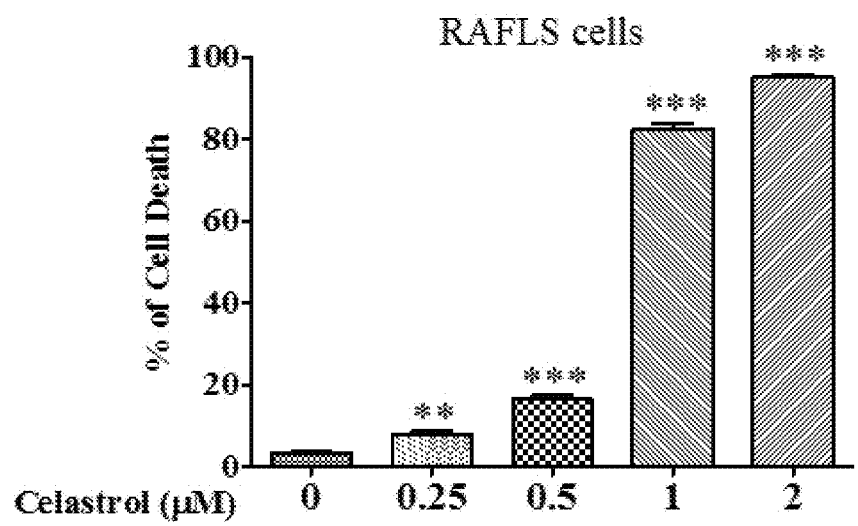
FIG. 3B shows the percentage of cell death of RAFLS after treatment of 0, 0.25, 0.5, 1 or 2 μM celastrol for 24 h. Data from the bar chart represented the mean values±S.D. of three independent experiments; error bars, S.D. ***, P<0.001.

Although synovial fibroblasts from RA are commonly resistant to apoptosis, celastrol displayed considerable cytotoxicity against rheumatoid arthritis synovial fibroblasts (RASFs) and RAFLS. With reference to FIGS. 1A and 1B, celastrol induced autophagy in time-dependent manner. It gradually increased both the percentage of endogenous LC3-II red puncta formation as well as cytotoxicity in a dose-dependent manner in RAFLS, as shown in FIGS. 2A, 2B, 3A and 3B. These findings suggested that celastrol-mediated cell death in synovial fibroblasts directly correlates with the accumulation of autophagosome.

Example 2

Autophagy Induction Via Mobilization of Cytosolic Calcium

Intracellular cytosolic $Ca^{2+}$ dynamic was measured using the FLIPR Calcium 6 Assay Kit (Molecular Devices) according to the manufacturer's instructions. In brief, RASFs were plated at a density of 10000 cells per well in black wall/clear bottom 96-multiwell plates from Costar (Tewksbury, Mass., USA) and cultured for 24 h before treatment. After that, calcium 6 reagent was added directly to cells, and cells were incubated for an additional 2 h at 37° C. and 5% $CO_2$. Indicated concentrations of celastrol or thapsigargin were then added to the wells and immediately subjected to data acquisition on the SpectraMax Paradigm Multi-Mode Microplate Reader (Molecular Devices) at room temperature using a 1-s reading interval throughout the experiments.

Flow cytometry analysis was performed to determine the cytosolic calcium level. Intracellular free calcium was measured by a fluorescent dye, Fluo-3. Briefly, RAFLS were washed twice with DMEM media after Celastrol treatment (1 µM) for 4 h. Then cell suspensions were incubated with 5 µM Fluo-3 at 37° C. for 30 min. Then the cells were washed twice with HBSS. After re-suspended cell samples were subjected to FACS analysis. At least 10,000 events were analyzed.

To determine the endogenous expression of LC3-II, RAFLS were treated with indicated concentrations of celastrol in the presence or absence of BAPTA/AM (BM) for 24 h. The cells were then fixed and visualised by fluorescence microscopy after staining with an LC3-II antibody followed by TRITC-conjugated anti-mouse secondary antibody.

In a detection of autophagic marker protein LC3 conversion, after celastrol treatments with or without the calcium chelator, BAPTA/AM (BM), RASFs were harvested and lysed in RIPA buffer (Cell Signaling Technologies Inc. (Beverly, Mass.). The cell lysates were then resolved by SDS-PAGE. After electrophoresis, the proteins from SDS-PAGE were transferred to nitrocellulose membrane which was then blocked with 5% non-fat dried milk for 60 minutes. The membrane was then incubated with LC3 primary antibodies (1:1000) in TBST overnight at 4° C. After that, the membrane was further incubated with HRP-conjugated secondary antibodies for 60 minutes. Finally, protein bands were visualized by using the ECL Western Blotting Detection Reagents (Invitrogen, Paisley, Scotland, UK).

Annexin V flow cytometry analysis was performed. Cell death and viability are measured using an Annexin V staining kit (BD Biosciences, San Jose, Calif., USA). Briefly, RAFLS are treated with 1 or 2 µM celastrol in the presence or absence of autophagic inhibitor, 3-MA or calcium chelator, BAPTA/AM (BM) for 24 h. Cells are then harvested and analysed by multiparametric flow cytometry using FITC-Annexin V and Propidium iodide staining (BD Biosciences, San Jose, Calif., USA) according to the manufacturer's instructions. Flow cytometry is then carried out using a FACSCalibur flow cytometer (BD Biosciences, San Jose, Calif., USA). Data acquisition and analysis is performed with CellQuest (BD Biosciences, San Jose, Calif., USA). Data are obtained from three independent experiments.

Figure 4:
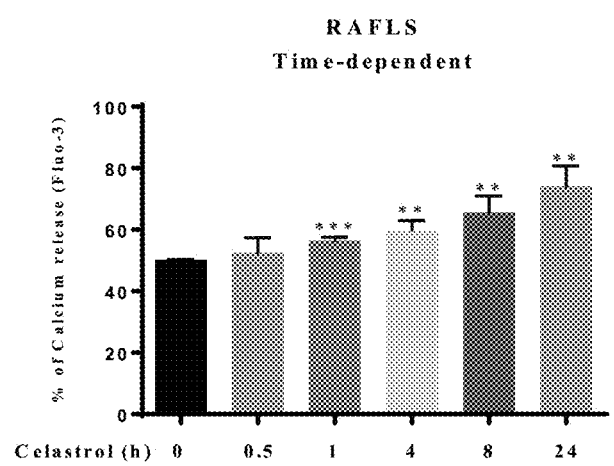
FIG. 4 shows the results obtained from flow cytometry analysis of RAFLS treated with or without 1 μM celastrol for 0-24 h. RAFLS treated with or without celastrol were stained with Fluo-3 dye prior to flow cytometry analysis. These results demonstrate that celastrol time-dependently mobilize the calcium release in RAFLS.
Figure 5:
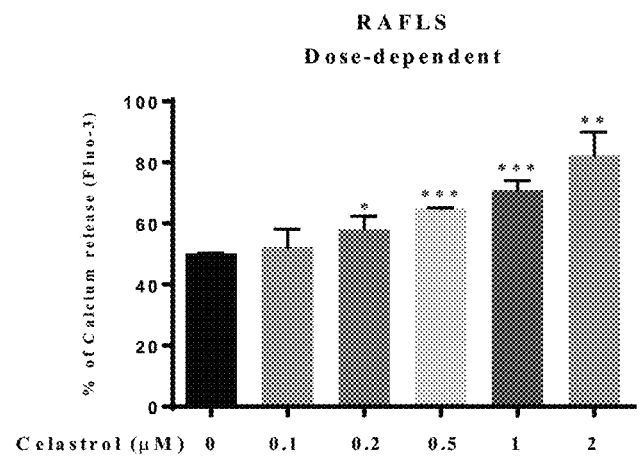
FIG. 5 shows the results obtained from flow cytometry analysis of RAFLS treated with 0, 0.1, 0.2, 0.5, 1 and 2 μM of celastrol for 4 h. After treatment, RAFLS were stained with Fluo-3 dye prior to flow cytometry analysis. These results demonstrate that celastrol dose-dependently mobilize the calcium release in RAFLS.

The inventors investigated the celastrol-mobilized calcium level in synovial fibroblasts from RA using flow cytometry analysis with Fluo-3 dye staining. With references to FIGS. 4 and 5, The calcium mobilization was determined with flow cytometry analysis using Fluo 3-AM in celastrol-treated RAFLS, suggesting that celastrol time and dose-dependently disturbs calcium homeostasis in the RASFs and RAFLS.

Figure 6:
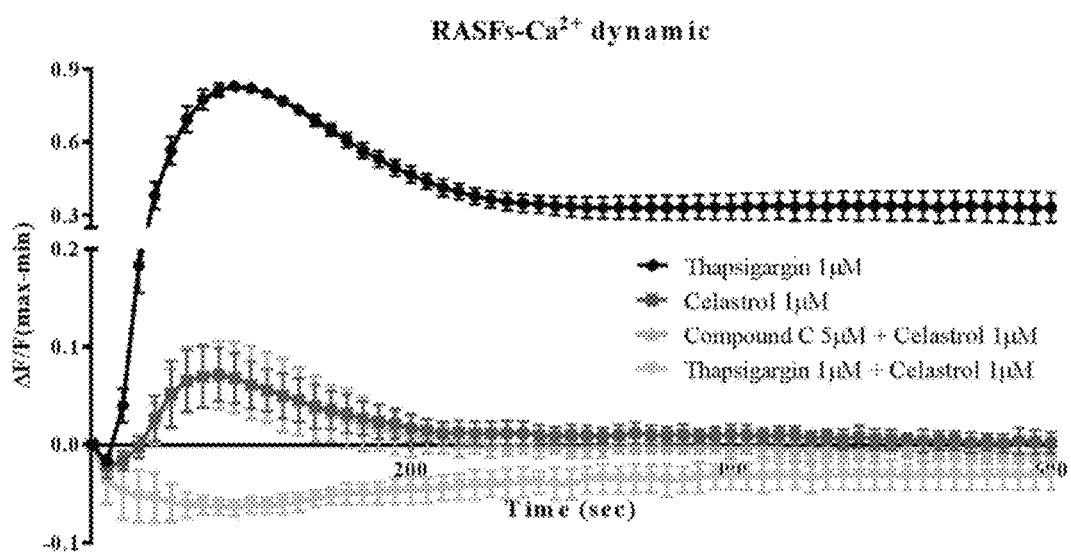
FIG. 6 is a calcium signaling chart showing the calcium dynamic changes in RASFs after treatment of 1 μM thapsigargin (a SERCA inhibitor), 1 μM celastrol, 5 μM Compound C (an AMPK inhibitor) and 1 μM celastrol, or 1 μM thapsigargin and 1 μM celastrol. RASFs were stained with FLIPR Calcium 6 Assay Kit before the treatments. After treatments, calcium dynamic in RASFs was measured by SpectraMax Paradigm. Data from the chart represented mean values±S.D. of three independent experiments; error bars, S.D. The results demonstrate that celastrol may target on SERCA for calcium mobilization.

The inventors further investigated whether celastrol may also inhibit SERCA for calcium dynamic change. According to the results shown in FIG. 6, SERCA inhibitor, thapsigargin (TG) significantly induced the calcium dynamic change in RASFs, whereas celastrol stimulated relative weak calcium dynamic. In addition, AMPK inhibitor exhibited no inhibitory effect on celastrol-induced calcium dynamic change, whereas RASFs pretreated with thapsigargin probably shut down the SERCA activity and showed extremely low response in calcium mobilization upon celastrol treatment, suggesting that celastrol probably targets on SERCA for calcium mobilization.

Figure 7A:
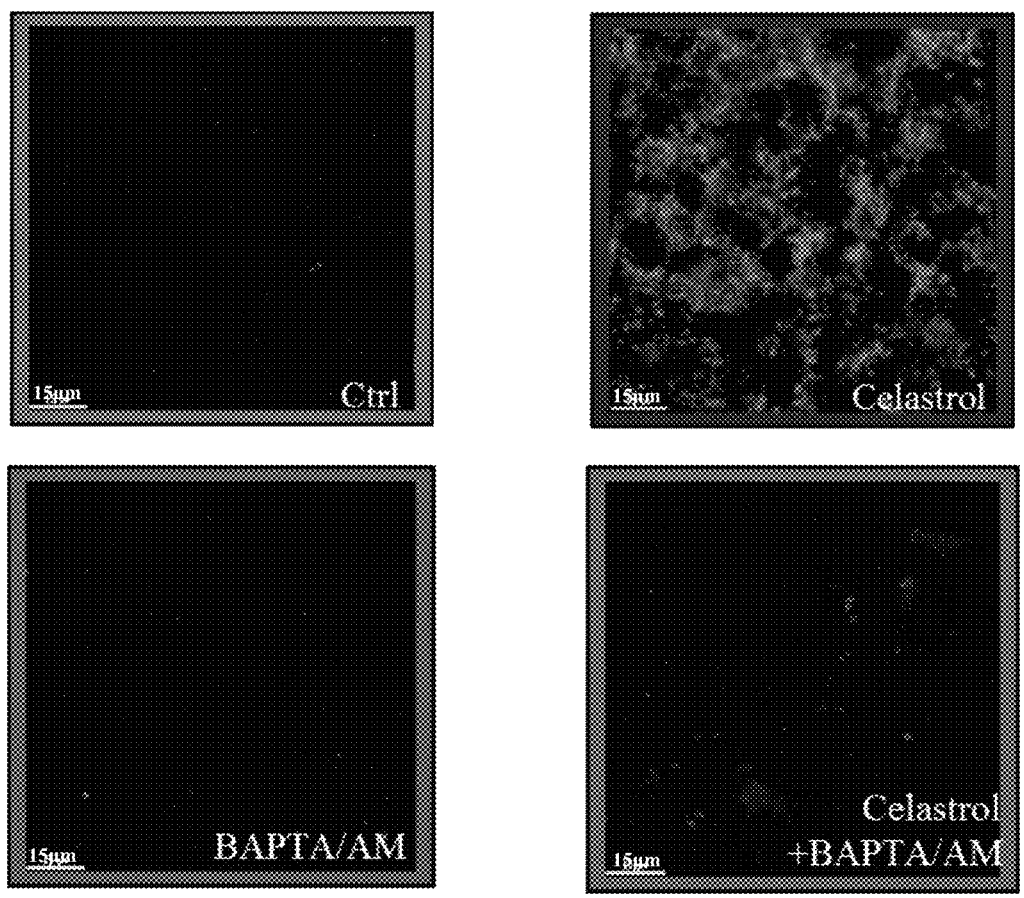
FIG. 7A shows fluorescence images obtained from immunocytochemistry imaging of RAFLS after treatment of DMSO, 1 μM celastrol, 10 μM calcium chelator BAPTA/AM, or 1 μM celastrol and 10 μM BAPT/AM for 24 h. Fluorescence images were captured at 60×magnification; scale bar, 15 μm. The results demonstrate that the calcium chelator BAPTA/AM abolished celastrol-induced autophagic effect in RAFLS.
Figure 7B:
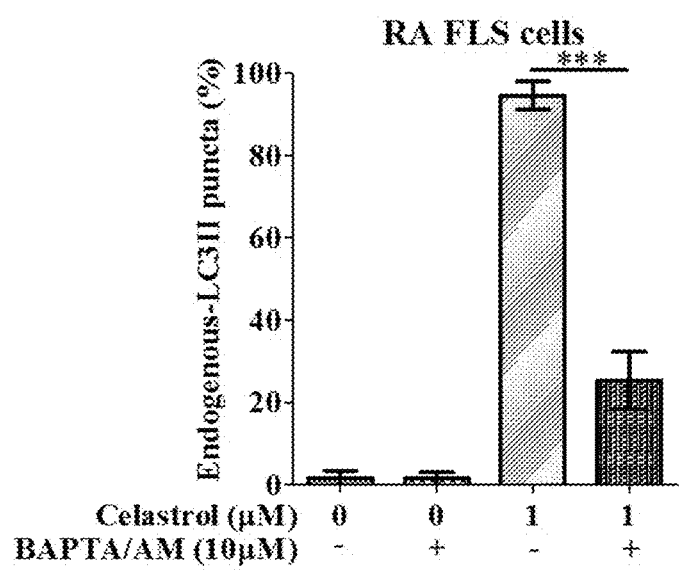
FIG. 7B is a bar chart showing the percentage of RAFLS expressing endogenous LC3-II puncta after treatment of 0 or 1 μM celastrol in the presence or absence of 10 μM BAPTA/AM.
Figure 8:
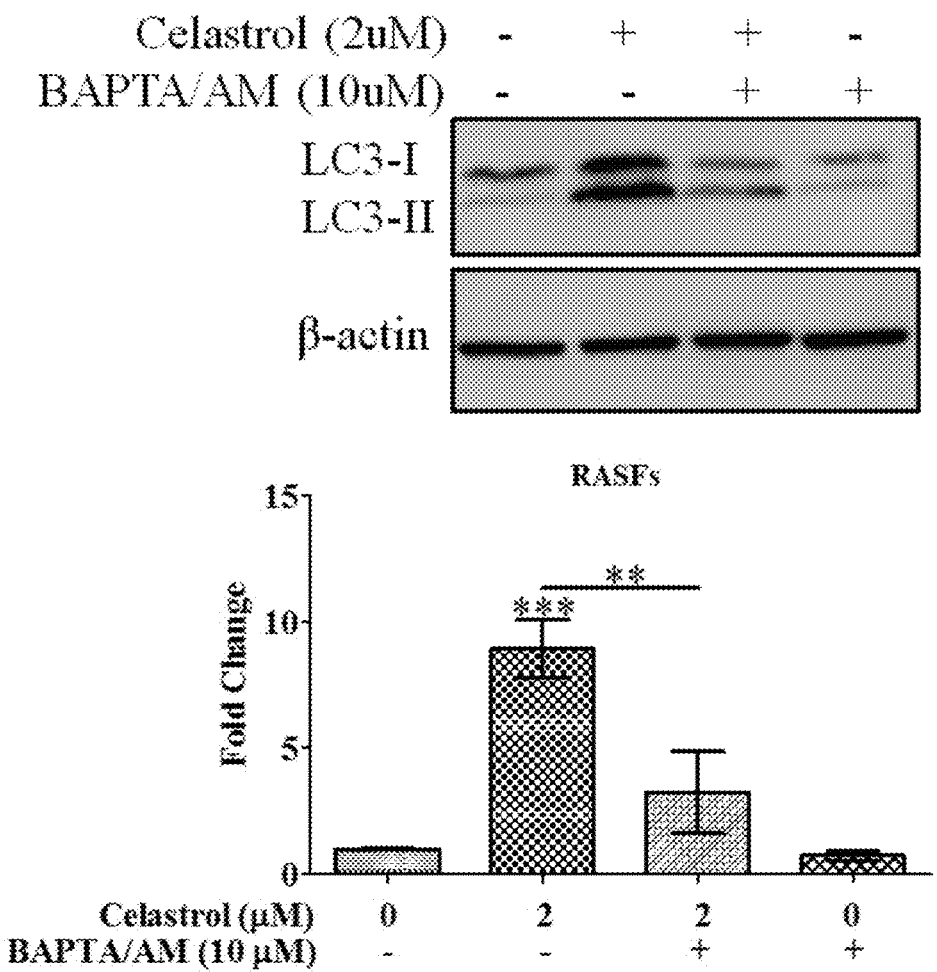
FIG. 8 shows the Western blot patterns of the expression of LC3-I and LC3-II (LC3-I, 18 kDa; LC3-II, 16 kDa) in RASFs treated with of 0 or 2 μM celastrol in the presence or absence of 10 μM BAPTA/AM. It also includes a bar chart showing quantitation of the fold change of LC3 conversion in RASFs after treatments.
Figure 9A:
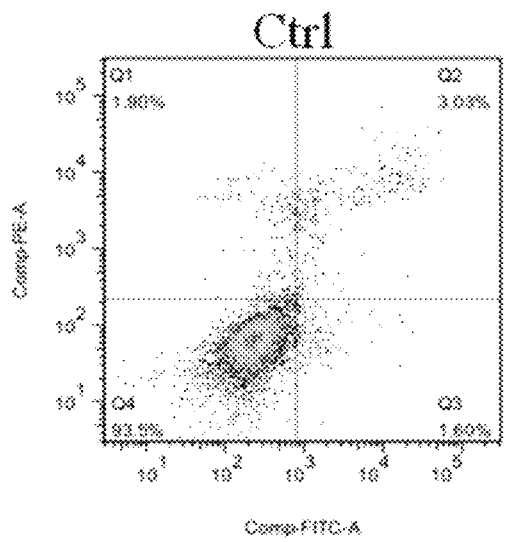
FIGS. 9A to 9G show the flow cytometry data obtained after treating RAFLS with DMSO (Control group), 5 mM 3-methyladenine (3-MA), 5 μM BAPTA/AM (BM), 1 μM celastrol, 2 μM celastrol, 2 μM celastrol and 5 mM 3-MA, or 2 μM celastrol and 5 μM BM. Celastrol-induced cell death was measured by flow cytometry analysis after annexin V staining.
Figure 9B:
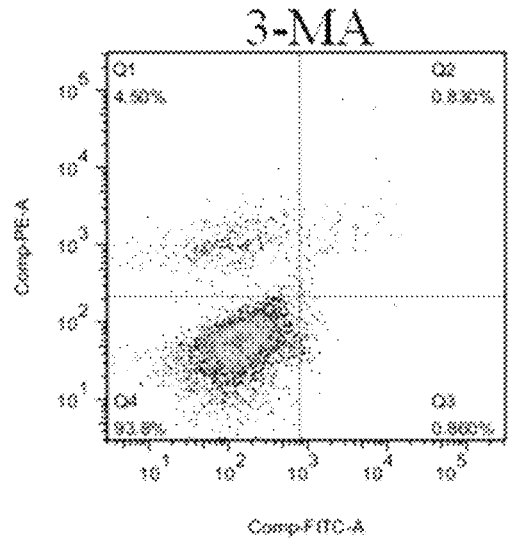
Figure 9C:
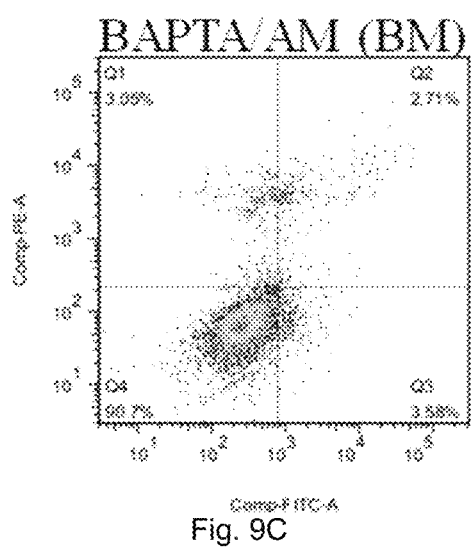
Figure 9D:
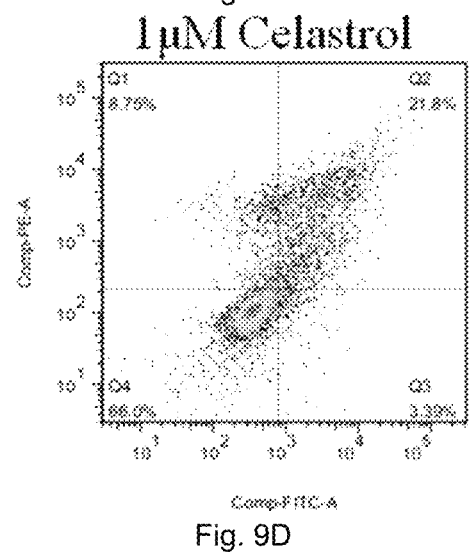
Figure 9E:
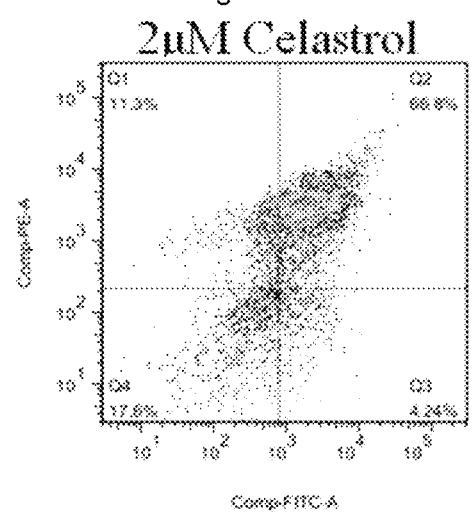
Figure 9F:
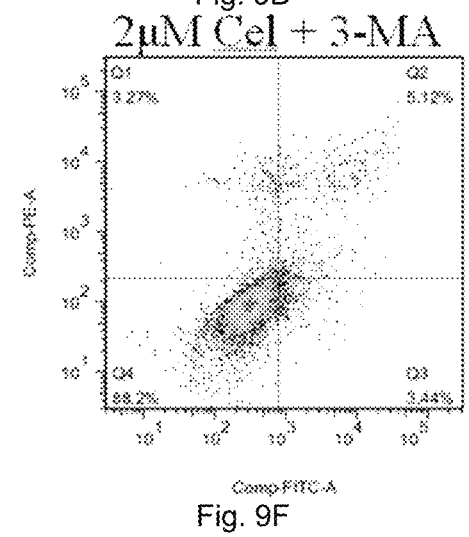
Figure 9G:
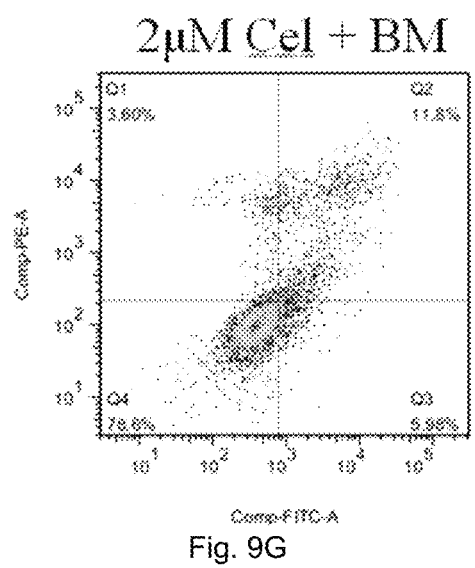
Figure 9H:
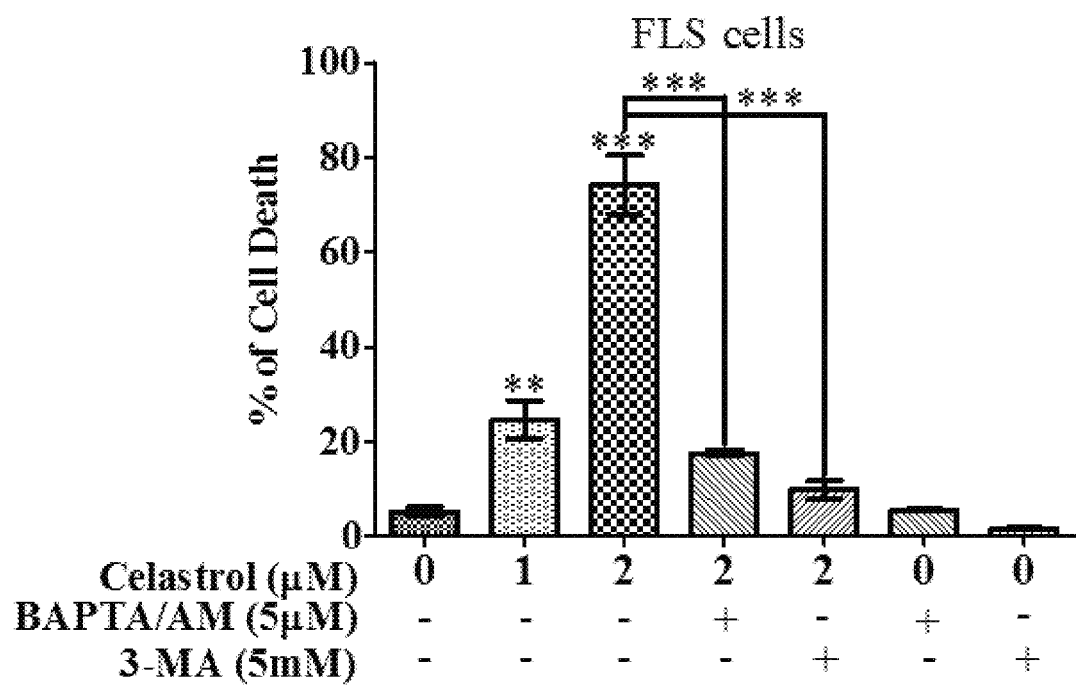
FIG. 9H is a bar chart showing the percentage of cell death after the aforesaid treatments on RAFLS. Data from the bar chart represented mean values±S.D. of three independent experiments; error bars, S.D. , P<0.01; *, P<0.001. The results demonstrate that BAPTA/AM and 3-MA reduced celastrol-mediated autophagic cell death in RAFLS.

As shown in FIGS. 7A and 7B, $Ca^{2+}$ chelator (BAPTA/AM) dramatically suppressed celastrol-induced endogenous LC3-II puncta formation in RAFLS, as well as inhibited LC3-II conversion in RASFs, FIG. 8.

Annexin V analyses, as shown in FIGS. 9A to 9H, demonstrates that BAPTA/AM or autophagy inhibitor 3-MA completely abolished celastrol-mediated autophagic cell death. These findings supported that celastrol induces autophagy by increasing the free cytosolic calcium ($[Ca^{2+}]c$) via SERCA inhibition, and implicates a role of $[Ca^{2+}]c$ in celastrol-induced autophagic cell death in RASFs and RAFLS.

Example 3

Inhibitory Effect of Celastrol on Apoptosis-Deficient RAFLS

The RAFLS transfected with mutants p53 were lysed with RIPA lysis buffer. Protein concentrations were determined using the Bio-Rad protein assay (Bio-Rad Laboratories, Inc., Hercules, Calif., USA). The cell lysates of samples were subjected to electrophoresis on SDS polyacrylamide gels and transferred to Hybond enhanced chemiluminescence nitrocellulose membranes (Amersham Biosciences, Piscataway, N.J.), which were then blocked with 5% non-fat dry milk protein for 1 hrs. Membranes were then incubated with the apoptotic marker antibodies overnight at 4° C. The binding of the antibody was visualized by peroxidase-coupled secondary antibody using the ECL Western Blotting Detection Reagents (Invitrogen, Paisley, Scotland, UK). Band intensities were quantified by using the software ImageJ (NIH, Bethesda, Md., USA).

Cytotoxicity Assays were performed. All test compounds were dissolved in DMSO at final concentrations of 50 mmol/L and stored at −20° C. before use. Cytotoxicity was assessed using the 3-(4, 5-dimethylthiazol-2-yl)-2, 5-diphenyltetrazolium bromide (MTT) (5.0 mg/ml) assay. Briefly, $4 \times 10^3$ RAFLS cells transfected with mutants p53 were seeded per well in 96-well plates before drug treatment. After overnight culture, the cells were then exposed to different concentrations of test compounds (0.039-100 μmol/L) for 72 h. Cells without drug treatment were used as control. Subsequently, MTT (10 μL) was added to each well and incubated at 37° C. for 4 hours followed by the addition of 100 μL solubilization buffer (10% SDS in 0.01 mol/L HCl) and overnight incubation. $A_{570}$ nm was determined from each well on the next day. The percentage of cell viability was calculated using the following formula: Cell viability (%)=$A_{treated}/A_{control} \times 100$. Data were obtained from triplication independent experiments.

Figure 10A:
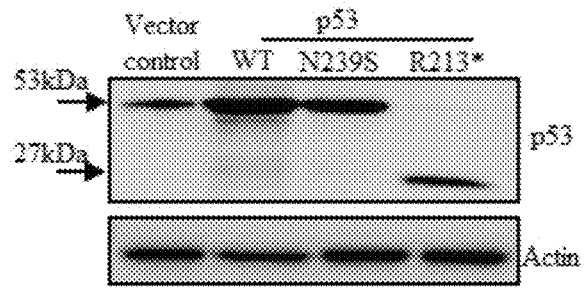
FIG. 10A shows Western blot patterns of p53 in RAFLS transfected with p53 mutants (N239S and R213*), in wild-type RAFLS and in control group.
Figure 10B:
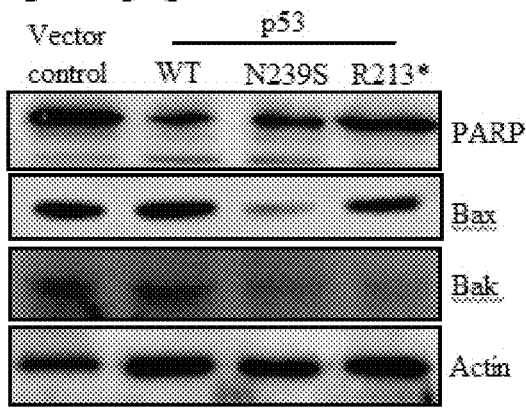
FIG. 10B shows Western blot patterns of pro-apoptotic markers including PARP, Bax, and Bak in RAFLS transfected with p53 mutants (N239S and R213*), in wild-type RAFLS and in control group.
Figure 10C:
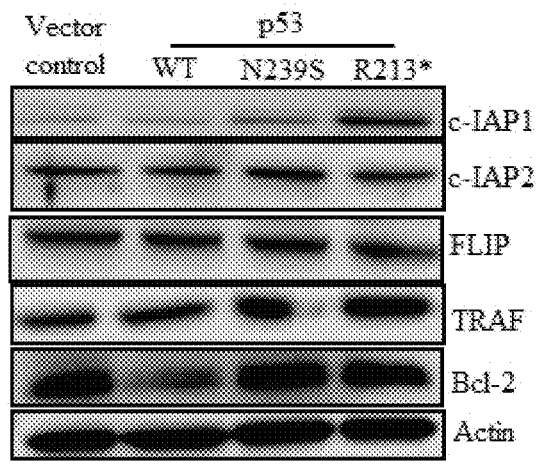
FIG. 10C shows Western blot patterns of anti-apoptotic markers including c-IAP1, TRAF and Bcl-2 in RAFLS transfected with p53 mutants (N239S and R213*), in wild-type RAFLS and in control group.

Clinical studies reported that a significant number of somatic mutations on p53 tumor suppressor gene were identified in synovium of rheumatoid arthritis patients. Some of these dominant-negative p53 mutations were correlated with inflammatory cytokine production and apoptotic mediator, Bax suppression, which may further potentiate the development of refractory RA. The inventors therefore overexpressed the RA hotspot p53 mutants N239S and R213* in RAFLS and determined the apoptotic markers expression. As expected, as shown in FIGS. 10A to 10c, the apoptotic markers, PARP, Bax and Bak were down-regulated in p53 mutants transfected RAFLS, whereas the anti-apoptotic markers, c-IAP1, TRAF and Bcl-2 were up-regulated, suggesting the developed apoptosis-resistant phenotypes of RAFLS in the presence of mutant p53. Nevertheless, celastrol demonstrated the same cytotoxic potency on these RAFLS with or without transfected p53 mutants, whereas the p53 mutant RAFLS showed resistance to methotrexate, as shown in Table 1. These results suggest that celastrol suppresses the apoptosis-resistant RAFLS independent to p53 status.

TABLE 1

Cytotoxicity tests results showing the resistance of RAFLS transfected with p53 mutants toward methotrexate and celastrol.

| RAFLS | Ctrl p53 WT | p53 N239S | p53 R213* |
|---|---|---|---|
| Methotrexate, mean IC$_{50}$ | 301 μM | 722 μM | >1000 μM |
| Resistant factor, RF | RF: 1 | RF: 2.4 | RF: >3.32 |
| Celastrol, mean IC$_{50}$ | 0.996 μM | 1.01 μM | 0.722 μM |
| Resistant factor, RF | RF: 1 | RF: 1.01 | RF: 0.72 |

Example 4

Inhibition on P-Glycoprotein in P-Glycoprotein Dependent RAFLS

RT-PCR was used to determine the P-gp level in both normal and RA patients. Human lymphocytes were isolated from peripheral blood by Ficoll-Paque plus (GE Healthcare life sciences). Isolation of total RNA from lymphocytes was processed using the Trizol reagent (Ambion, Carlsbad, Calif., USA). The RNA concentration was evaluated by absorbance readings using a Nano-Drop2000 spectrophotometer (Thermo Scientific, Fremont, Calif., USA). Reverse transcription of RNA was carried out with the Transcriptor Universal cDNA Master (Roche, USA). Real-time-PCR for ABCB5 mRNA was performed using the Applied Biosystems ViiA™ 7 Real-Time PCR System (ABI, USA) and the cDNA amplifications were monitored by the measurement of the SYBR Green fluorescence; Real-time PCR was conducted in a total volume of 20 μL: containing 2 μL of cDNA, 0.3 μL of forward primer (10 μM), 0.3 μL of the reverse primer (10 μM), 10 μL of SYBR select Master Mix (ABI, Austin, Tex., USA), Sterile water was added to the reaction mix. PCR reaction was initiated after a 10 mins denaturation at 95° C., followed by 40 cycles of 15 seconds denaturation at 95° C., 60 seconds annealing at 60° C.

```
                              (SEQ ID NO: 1)
Hu-ABCB5-F:     ATGTACAGTGGCTCCGTTCC (SEQ ID NO: 2)
Hu-ABCB5-R:     ACACGGCTGTTGTCACCATA
```

All test compounds were dissolved in DMSO at final concentrations of 50 mmol/L and stored at −20° C. before use. Cytotoxicity was assessed using the 3-(4, 5-dimethylthiazol-2-yl)-2, 5-diphenyltetrazolium bromide (MTT) (5.0 mg/ml) assay. Briefly, $4 \times 10^3$ RAFLS cells overexpressed with P-gp were seeded per well in 96-well plates before drug treatment. After overnight culture, the cells were then exposed to different concentrations of test compounds (0.039-100 μmol/L) for 72 h. Cells without drug treatment were used as control. Subsequently, MTT (10 μL) was added to each well and incubated at 37° C. for 4 hours followed by the addition of 100 μL solubilization buffer (10% SDS in 0.01 mol/L HCl) and overnight incubation. $A_{570}$ nm was determined from each well on the next day. The percentage of cell viability was calculated using the following formula: Cell viability (%)=$A_{treated}/A_{control} \times 100$. Data were obtained from triplication independent experiments.

Activity of P-gp ATPase in response to celastrol or verapamil was determined by Pgp-Glo assay system (Promega, Madison, Wis.). According to the manufacture instruction, the inhibitory effect of celastrol on the activity of P-gp ATPase was measured in the presence of verapamil (as a positive stimulator). The luminescence of the sample reflects the ATP level in the sample, which is negatively correlated with the activity of P-gp ATPase and was recorded using the SpectraMax Paradigm Multi-Mode Microplate Reader (Molecular Devices). DMSO-treated activities are expressed as the percentage of basal activity. By comparing basal activity to test compound-treated activities, the compounds can be ranked as stimulating, inhibiting, or having no effect on basal P-gp ATPase activity.

Rho123 exclusion assay was performed. P-gp overexpressing RAFLS were seeded in 6 well-plate at a final concentration of $2 \times 10^5$ cells @ well and cultured for 24 h at 37° C. in an atmosphere containing 5% $CO_2$. At confluence, 3 mL fresh media with or without 0.2, 0.5 and 1 µM celastrol, or 10 µM verapamil (known P-gp inhibitor) was added and incubated further at 37° C. for 24 h. Subsequently, 3 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 µL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

Annexin V flow cytometry analysis was performed. Cell death and viability are measured using an Annexin V staining kit (BD Biosciences, San Jose, Calif., USA). Briefly, RAFLS are treated with 0.1 or 0.2 µM celastrol in the presence or absence of 450 M methotrexate (MTX) for 24 h. Cells are then harvested and analysed by multiparametric flow cytometry using FITC-Annexin V and Propidium iodide staining (BD Biosciences, San Jose, Calif., USA) according to the manufacturer's instructions. Flow cytometry is then carried out using a FACSCalibur flow cytometer (BD Biosciences, San Jose, Calif., USA). Data acquisition and analysis is performed with CellQuest (BD Biosciences, San Jose, Calif., USA). Data are obtained from three independent experiments.

Figure 11:
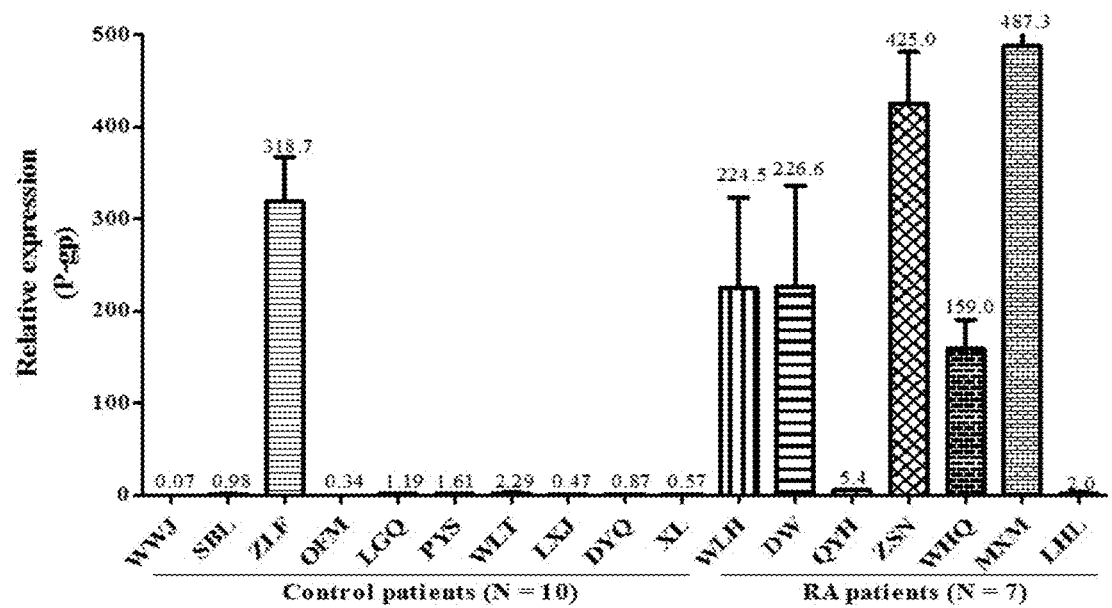
FIG. 11 is a bar chart showing the relative expression of P-glycoprotein (P-gp) in blood lymphocytes obtained from patients suffering from rheumatoid arthritis (RA) and those not suffering from RA.

Clinical studies reported that the RA patients treated with DMARDs would have higher percentage of P-gp expression in their peripheral blood lymphocytes, those patients would eventually develop drug-resistance with severe inflammatory condition. Referring to FIG. 11, the clinical data also supported these findings that 5 out of 7 RA patients showed high P-gp expression in their blood lymphocytes, whereas only 1 non-RA patient was found to have P-gp overexpression among 10 non-RA patients, suggesting that P-gp expression maybe commonly found in RA patients.

The inventors cloned and overexpressed the P-gp in RAFLS and determined the cytotoxic effect of celastrol. With reference to Table 2, P-gp overexpressing RAFLS showed cross-resistance to methotrexate, dexamethasone, prednisolone and colchicine at certain level, but not to celastrol, suggesting that celastrol is not excluded by P-gp activity.

TABLE 2

Cytotoxicity tests results showing the resistance of P-gp-dependent RAFLS toward MTX, DEX, prednisolone and celastrol.

| Drug | RAFLS | RAFLS p-gp over expression | Resistant Factor |
| --- | --- | --- | --- |
| Methotrexate (MTX) | 219 µM | 838 µM | 3.83 |
| Dexamethasone (DEX) | 600 µM | >2000 µM | 3.33 |
| Prednisolone | 123 µM | 216 µM | 1.76 |
| Colchicine | 11.3 µM | 46 µM | 4.07 |
| Celastrol | 1.3 µM | 1.45 µM | 1.12 |

Figure 12:
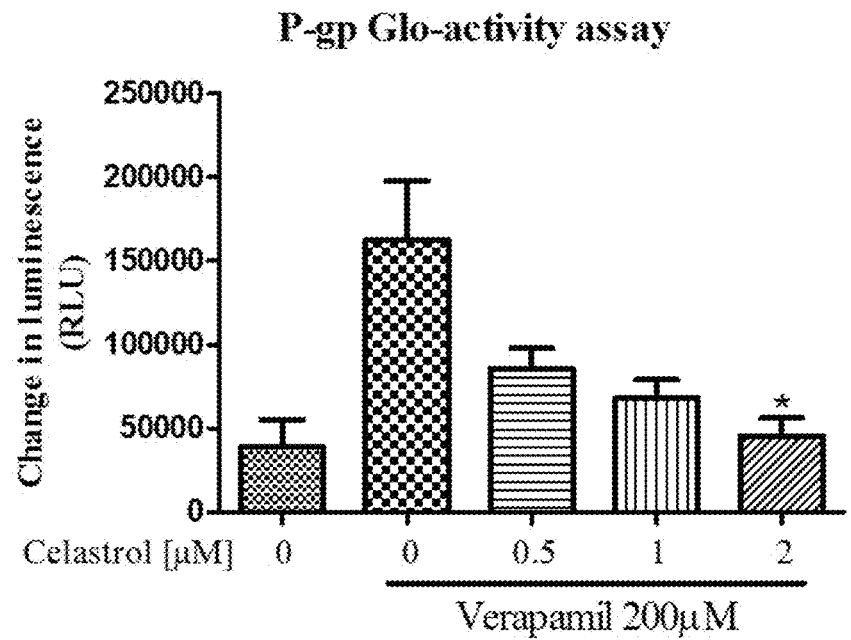
FIG. 12 shows the results obtained from P-gp Glo-activity assay using celastrol at a concentration of 0, 0.5, 1 or 2 μM, the activated form of P-gp and 200 μM verapamil. The results show that celastrol has a direct suppression effect on verapamil-activated P-gp activity. In the assay, celastrol was incubated with P-gp protein in the presence of 200 μM verapamil and ATP for 1 hour at 37° C. The luminescence was then measured by P-gp Glo™ Assay System. Change in luminescence (RLU) represented the activity of P-gp, whereas the activity shown in the control group indicated the basal P-gp ATPase activity.

P-gp Glo-activity assay further validated that celastrol directly suppresses the activated form of P-gp in dose-dependently manner, as shown in FIG. 12, concluding that celastrol is a novel P-gp inhibitor.

Figure 13A:
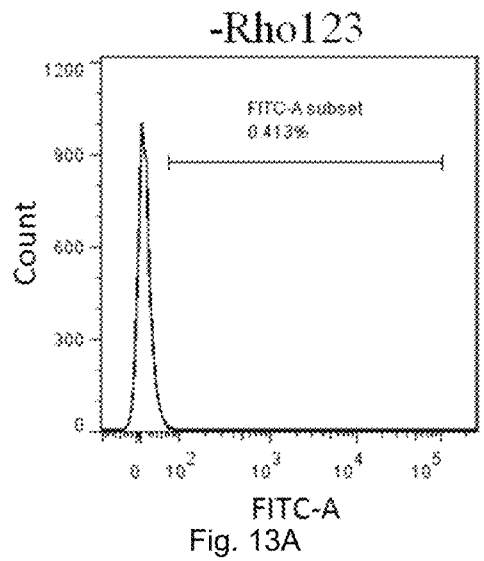
FIGS. 13A to 13H show the flow cytometry data obtained after incubating transfected RAFLS overexpressing P-gp with or without 10 μM verapamil, or with 0.1, 0.5 or 1 μM celastrol for 4 h at 37° C. After incubation, 3 μg/mL rhodamine 123 dye (Rho123) was added to each well and the wells were incubated for another 1 h at 37° C. The transfected RAFLS accumulated Rho123 were then measured by flow cytometer.
Figure 13B:
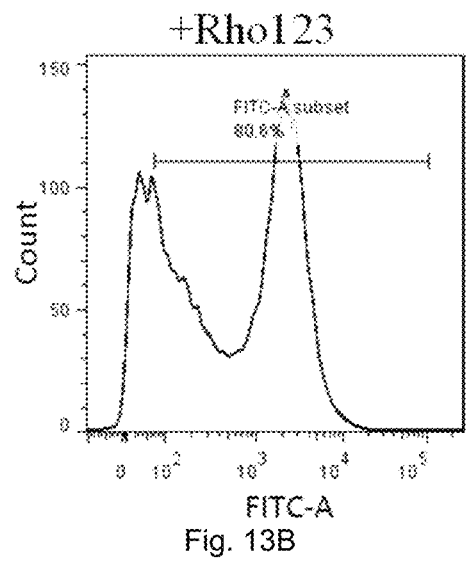
Figure 13C:
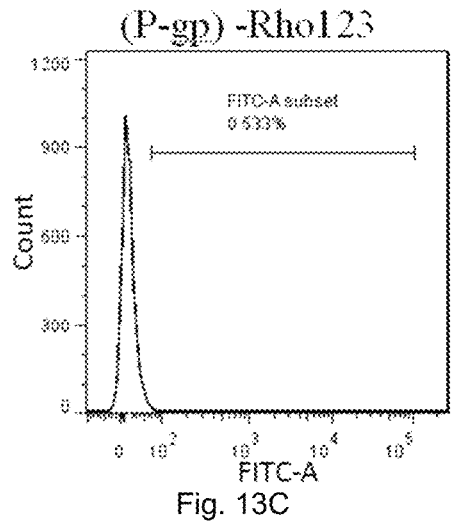
Figure 13D:
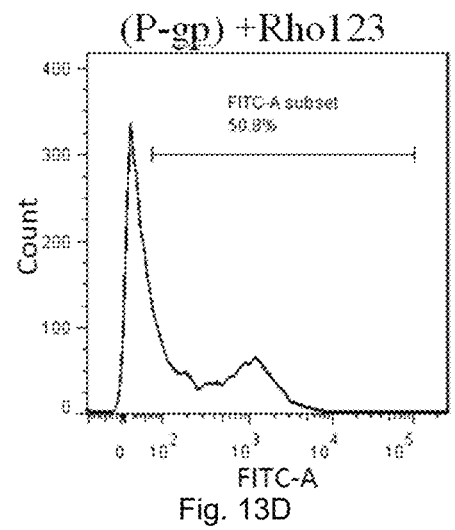
Figure 13E:
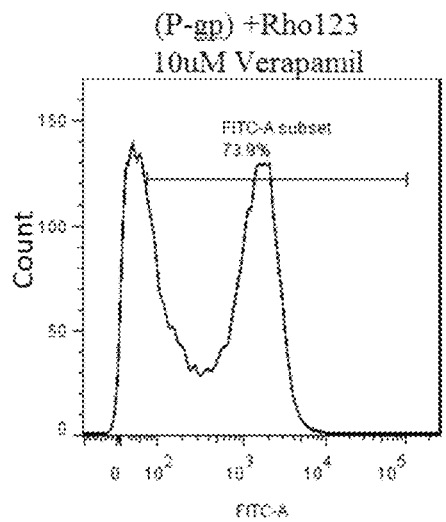
Figure 13F:
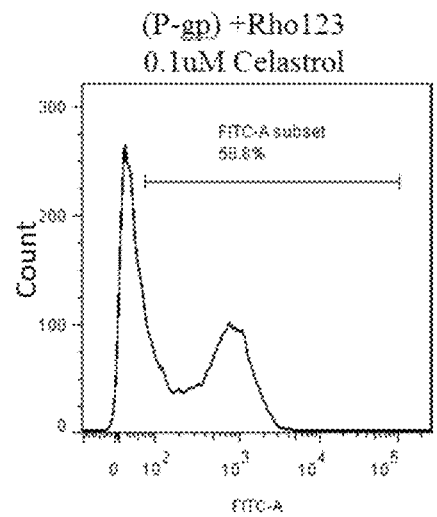
Figure 13G:
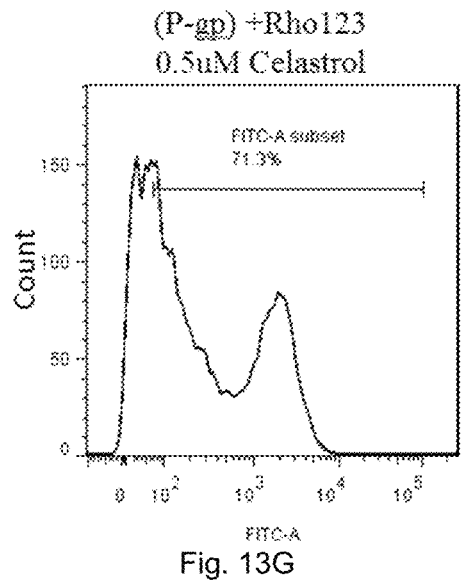
Figure 13H:
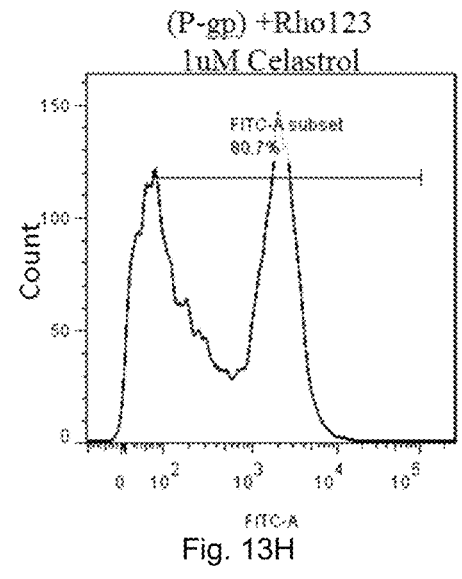
Figure 13I:
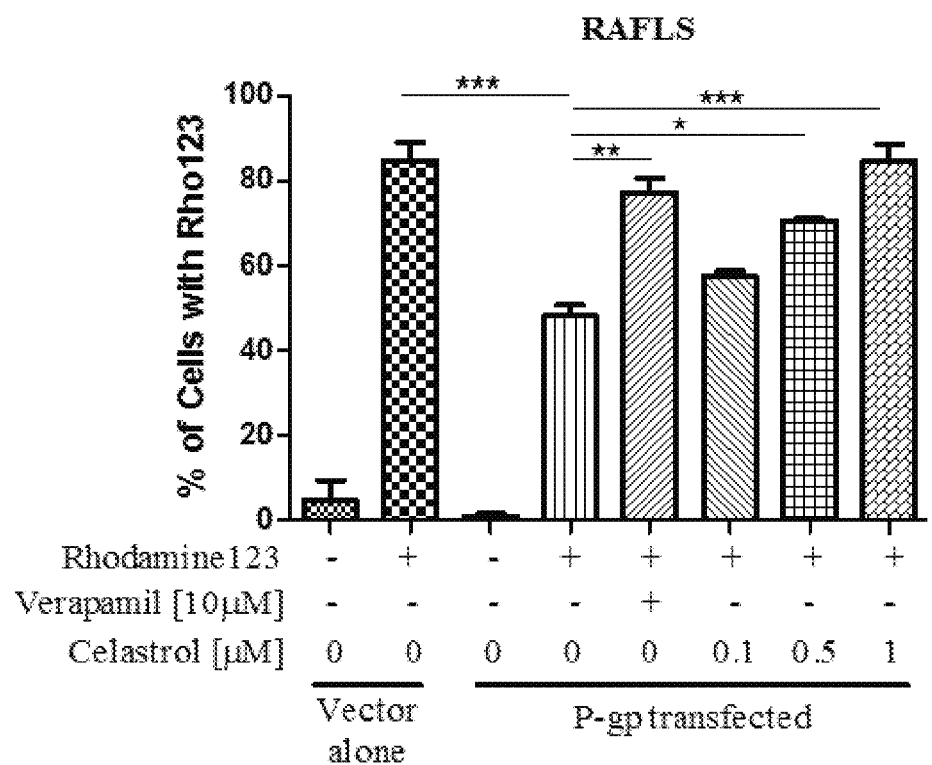
FIG. 13I is a bar chart showing the percentage of RAFLS accumulated with Rho123 after aforesaid treatments. The results from the Rho123 exclusion assay demonstrate that celastrol has inhibitory effect on P-gp activity.
Figure 14A:
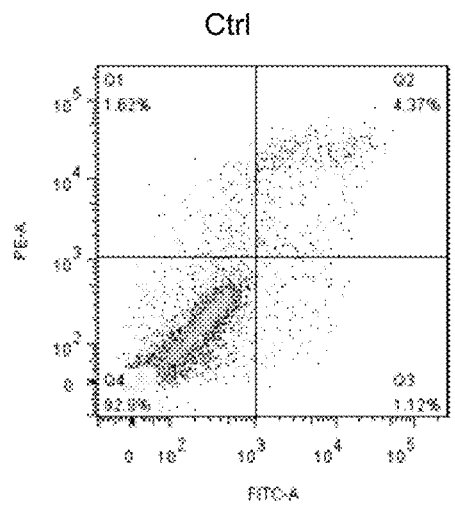
FIGS. 14A to 14F show the flow cytometry data obtained after treating RAFLS with DMSO (Control group), 450 μM methotrexate (MTX), 0.1 μM celastrol, 0.2 μM celastrol, 0.1 μM celastrol and 450 μM MTX, or 0.2 μM celastrol and 450 μM MTX. Celastrol-induced cell death was measured by flow cytometry analysis after annexin V staining.
Figure 14B:
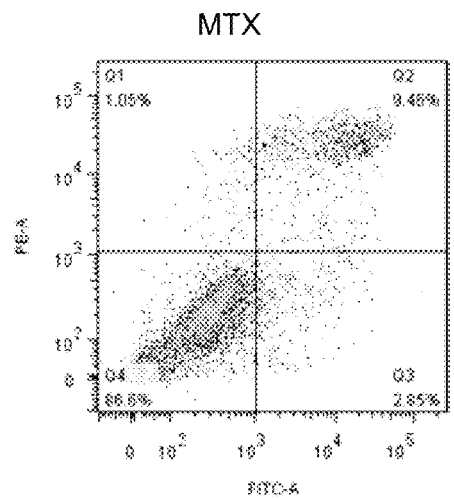
Figure 14C:
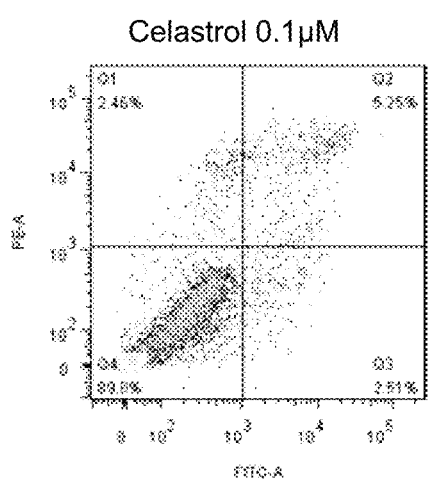
Figure 14D:
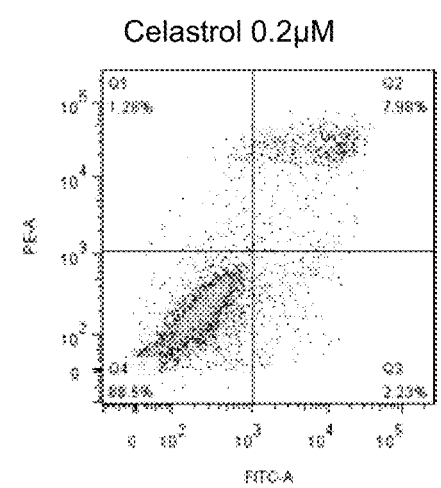
Figure 14E:
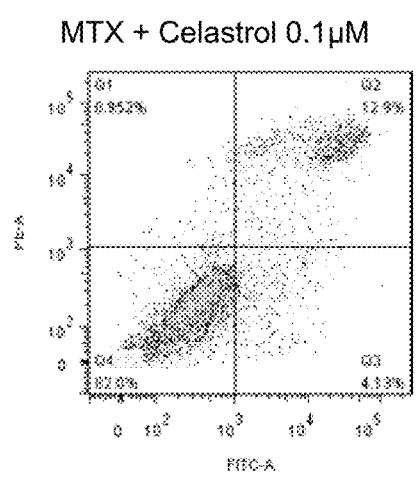
Figure 14F:
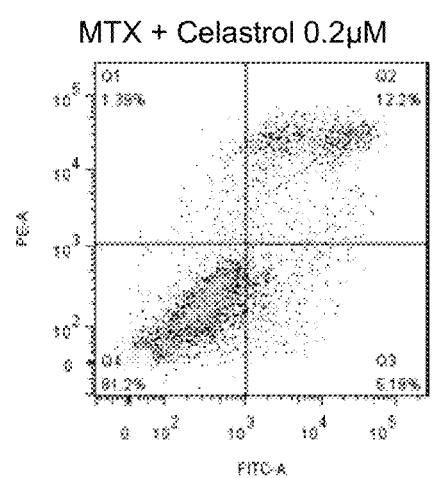
Figure 14G:
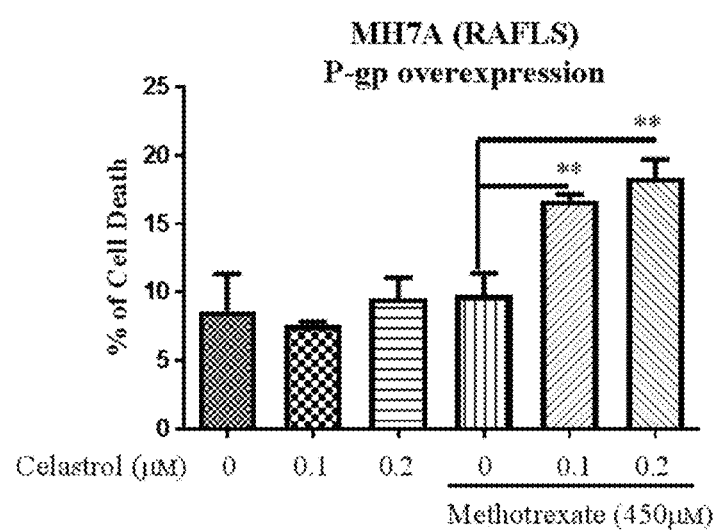
FIG. 14G is a bar chart showing the percentage of cell death after the aforesaid treatments on RAFLS. Data from the bar chart represented mean values±S.D. of three independent experiments; error bars, S.D. **, P<0.01. The results demonstrate that low dose of celastrol sensitized the MTX-mediated cell death in RAFLS.

In addition, the results from Rhodamine 123 (Rho123) functional assay, as shown in FIGS. 13A to 13H, indicated that more than 80% of RAFLS accumulated Rho123 dye under normal condition. When RAFLS transfected with P-gp expression construct, around 50% of P-gp overexpressing RAFLS accumulating Rho123, addition of P-gp inhibitor, verapamil increased accumulation of Rho123 with around 80%. Interestingly, relatively low doses of celastrol gradually increased Rho123 accumulation in a dose-dependent manner, FIG. 13I. Furthermore, non-toxic doses of celastrol (0.1-0.2 µM) suppressed the function of the overexpressed P-gp and prevented it from pumping out MTX, thereby potentiating the toxicity of MTX in the P-gp-overexpressing RAFLS (FIG. 14A to 14G). Collectively, celastrol is able to circumvent the MDR phenotype in drug-resistant RAFLS via direct inhibition of P-gp activity.

Example 5

Suppression on Adjuvant-Induced Arthritis (AIA) Condition Via Calcium Mobilization Adjuvant-induced arthritis (AIA) rat model was used. Experiments were performed using 6-week-old male Sprague Dawley (SD) rats at a weight of 130±20 g, which were purchased from Guangdong Medical Lab Animal Center. The animals were housed in a 12 h light/dark cycles and temperature-controlled room and given ad libitum access to food and water.

Arthritis was induced in rats by inoculation with complete Freund's adjuvant (CFA). Non-viable desiccated *Mycobacterium tuberculosis* (BD, USA) emulsified in mineral oil (Sigma, USA) with 5 mg/ml of *Mycobacterium tuberculosis*, grinding on the ice in a direction. Emulsions prepared with these adjuvants should have a consistency of dense whipped cream and not disperse quickly when a droplet of emulsion is placed on the surface of a water-filled beaker. Briefly, the rats were injected intradermally at the base of the tail with 100 µL emulsified oil. The first signs of inflammation were observed on day 9 after adjuvant injection. Arthritic score were evaluated and recorded every three days. Each paw were evaluated and scored individually with a scale from 0-4, the scoring criteria were as follows: 0, no evidence of erythema and swelling; 1, erythema and mild swelling confined to the tarsals or ankle joint; 2, erythema and mild swelling extending from the ankle to the tarsals; 3, erythema and moderate swelling extending from the ankle to metatarsal joints; 4, erythema and severe swelling encompass the ankle, foot and digits, or ankylosis of the limb.

50 male rats were randomly divided into 6 experimental groups as follows: (1) Healthy control group (n=8) without treatments; (2) Vehicle control group (n=10), AIA rats received the same vehicle and administration route of the drug correspondent in each experiment; (3) Positive control group (n=8), AIA rats were gavage-fed with MTX 7.6 mg/kg/week in a volume of 10 mL/kg bodyweight. (4) AIA rats were treated with 1 mg/kg of celastrol (cel) (n=8); (5) AIA rats were treated with 2 mg/kg of celastrol (cel) (n=8); (6) AIA rats were treated with 1 mg/kg of celastrol (cel)+3.5 mg/kg BAPTA/AM (BM) (n=8). AIA rats were treated with celastrol by i.p. for daily in the first 19 days, and then treated for every 2 days until days 36, whereas BM was treated in daily base. Celastrol (China Chengdu MUST, A0106) and BAPTA/AM (Santa cruz, USA) was diluted in the formula (PEG400: $H_2O$:Ethanol=6:3:1) and administered i.p. in a volume of 1 mL/kg bodyweight. Methotrexate (MTX) was dissolved in propylene glycol, tween-80 and normal saline in ratio of 50:5:45.

The left hind paw was fixed in 4% PFA, and scanned using in vivo micro-CT scanner (SkyScan 1176, Bruker, Belgium). The following scanning parameters were used to obtain high-quality images of the joint of the rat: 35 μm resolution, 85 kV, 385 μA, 65 ms exposure time, 0.7 rotation step in 360', and a 1 mm AI filter. The images were reconstructed using NRecon software (Bruker-micro CT, Belgium).

Figure 15A:
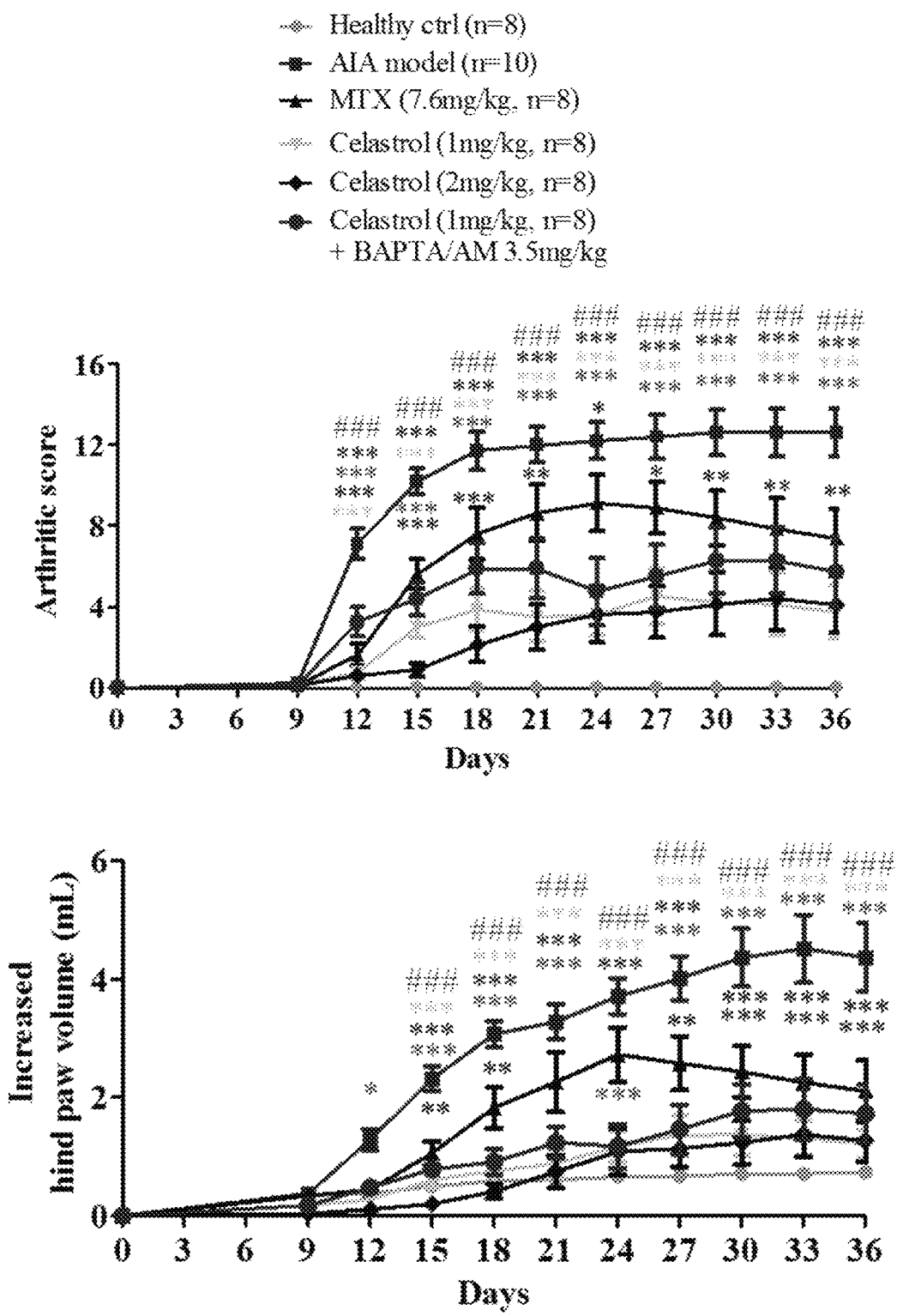
FIG. 15A shows the arthritic scores and increased hind paw volumes determined from 6 groups of rats respectively treated with vehicle, MTX (7.6 mg/kg), celastrol (1 and 2 mg/kg), or celastrol (1 mg/kg) combined with BAPTA/AM (3.5 mg/kg) after arthritis induction for 36 days. The arthritis induced animal model is called adjuvant-induced arthritis (AIA) model. The arthritic scores together with hind paw volumes (mL), and body weights were determined every 3 days, while the organs weight were calculated for each AIA rat at the end of the experiment. Data are expressed as means±SEM (n=8-10). *p<0.05, p<0.01, *p<0.001 compared to vehicle-treated AIA rats.
Figure 15B:
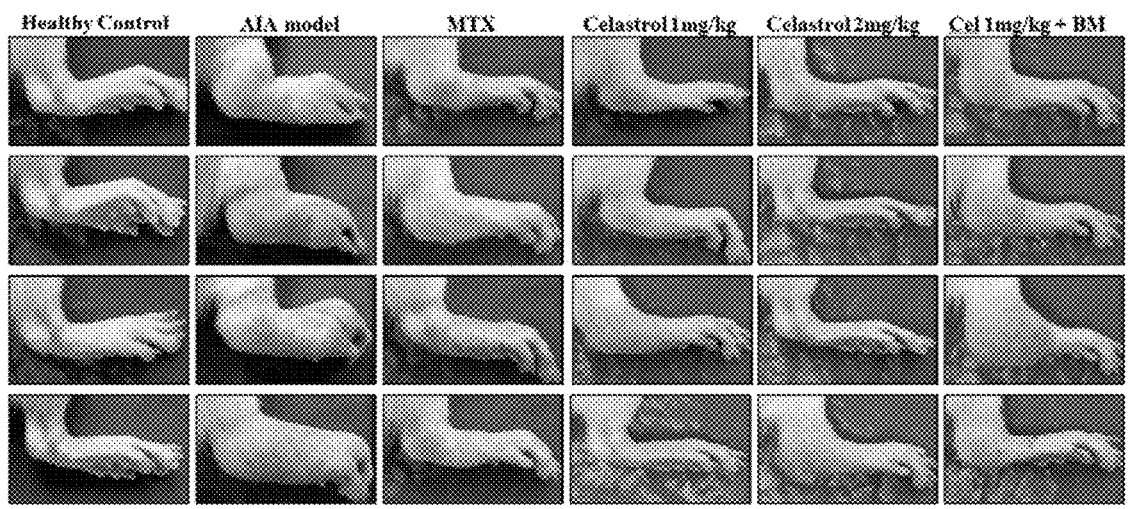
FIG. 15B shows the representative images of hind paw swelling of AIA rats after the aforesaid treatments.
Figure 16:
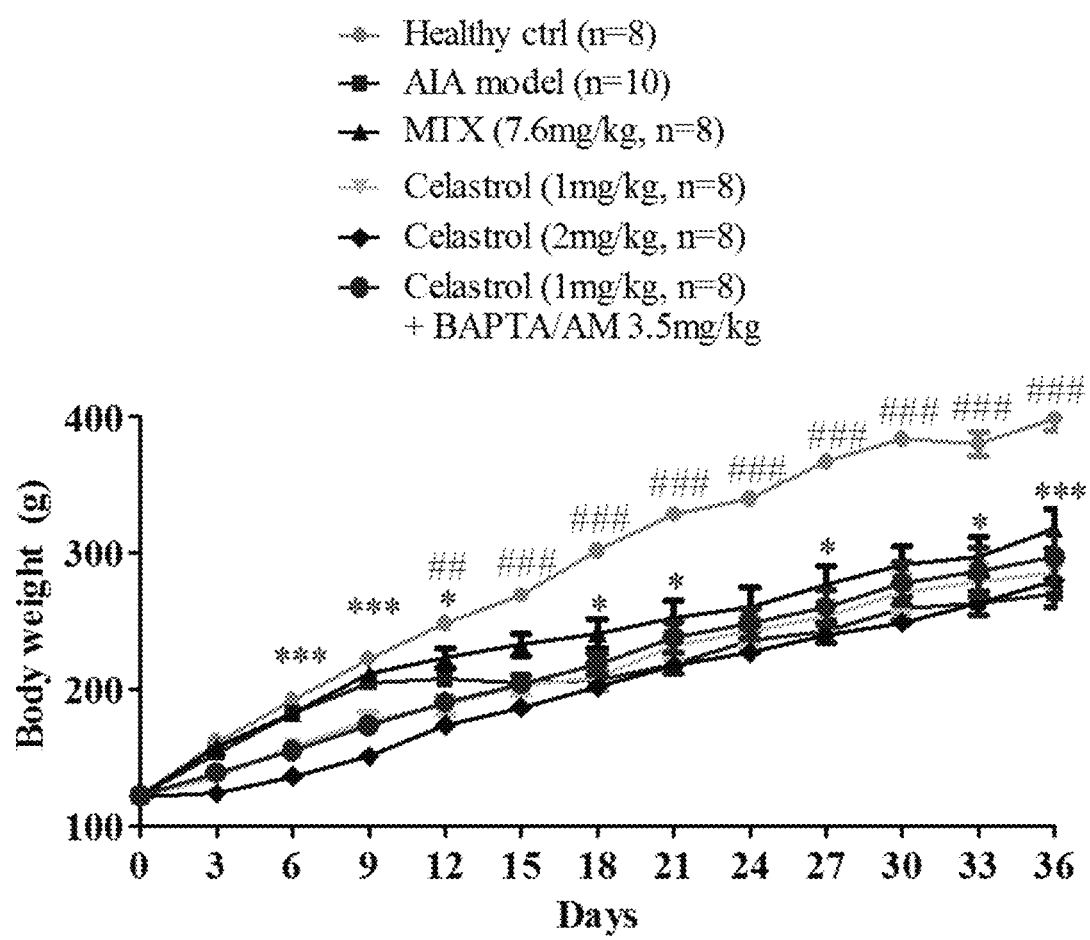
FIG. 16 shows the body weight of AIA rats after treatment of vehicle, MTX (7.6 mg/kg), celastrol (1 and 2 mg/kg), or celastrol (1 mg/kg) combined with BAPTA/AM (3.5 mg/kg) after arthritis induction for 36 days.
Figure 17A:
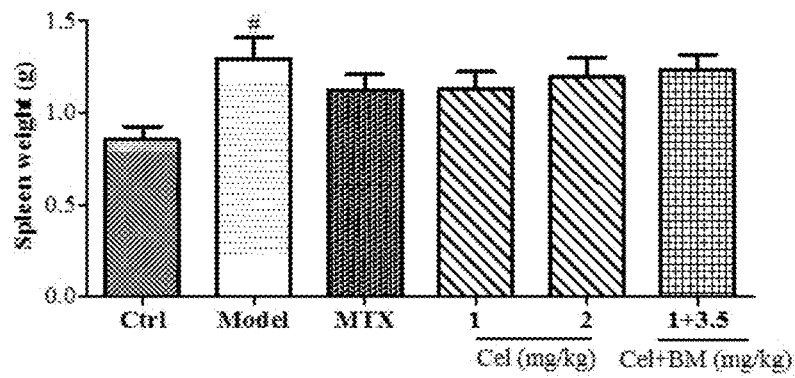
FIG. 17A to 17I show the organs weight of AIA rats after treatment of vehicle, MTX (7.6 mg/kg), celastrol (1 and 2 mg/kg), or celastrol (1 mg/kg) combined with BAPTA/AM (3.5 mg/kg) after arthritis induction for 36 days. The measured organs are spleen, brain, lung, adrenal, liver, heart, kidney, thymus and testis.
Figure 17B:
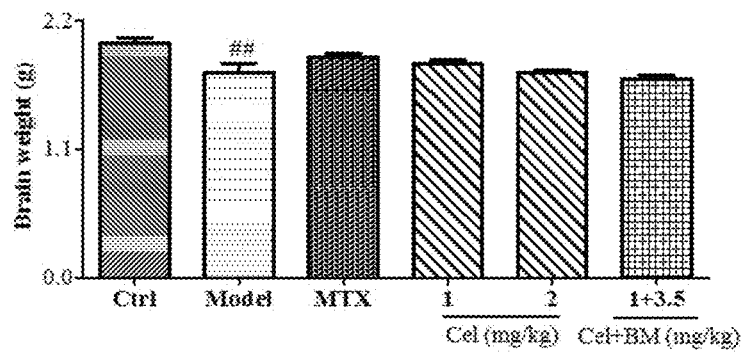
Figure 17C:
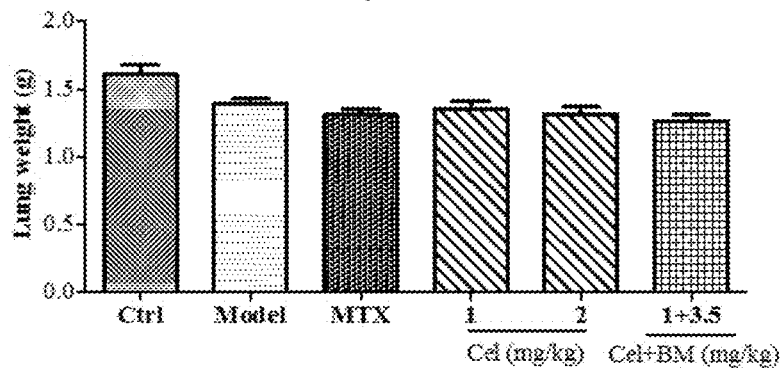
Figure 17D:
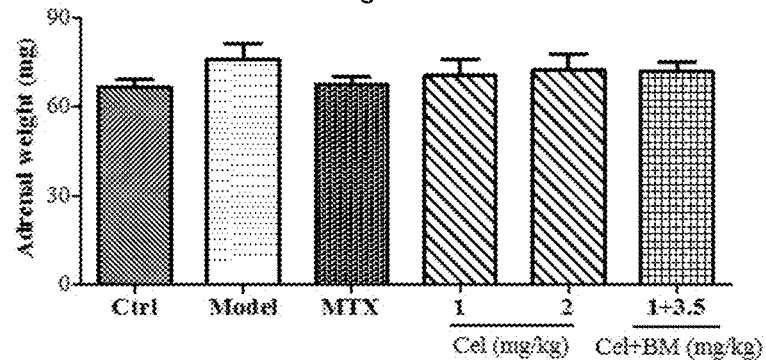
Figure 17E:
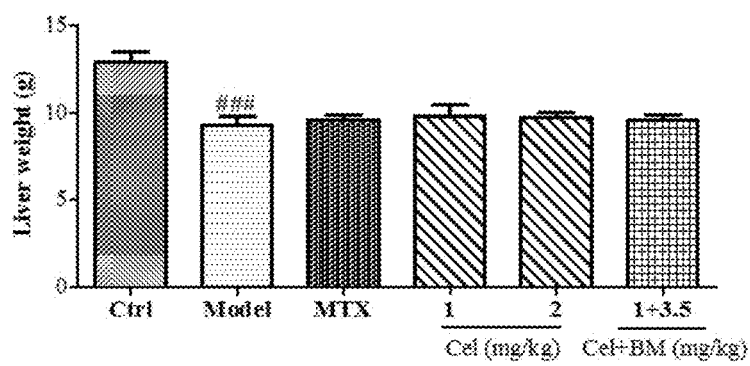
Figure 17F:
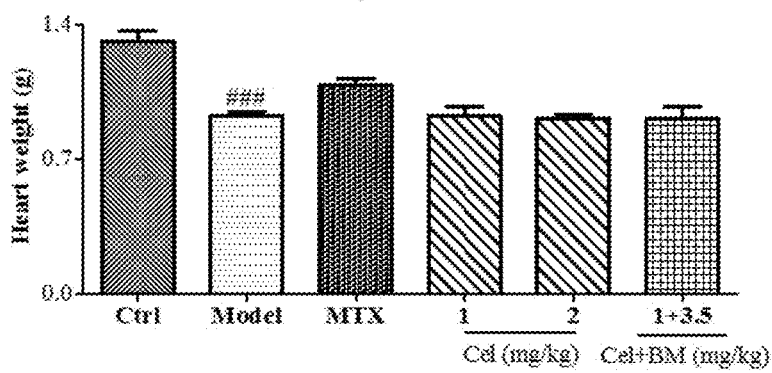
Figure 17G:
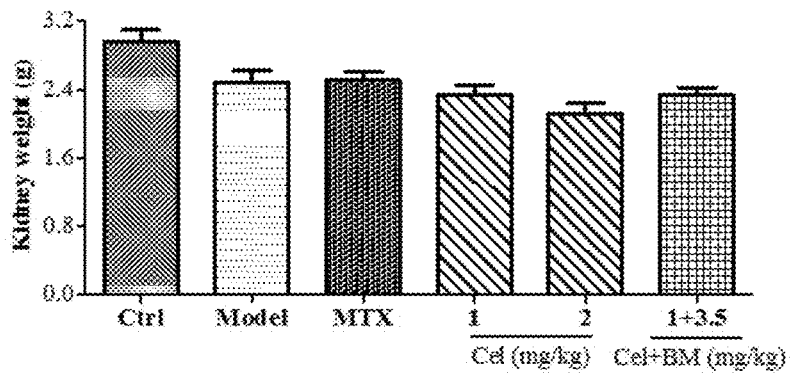
Figure 17H:
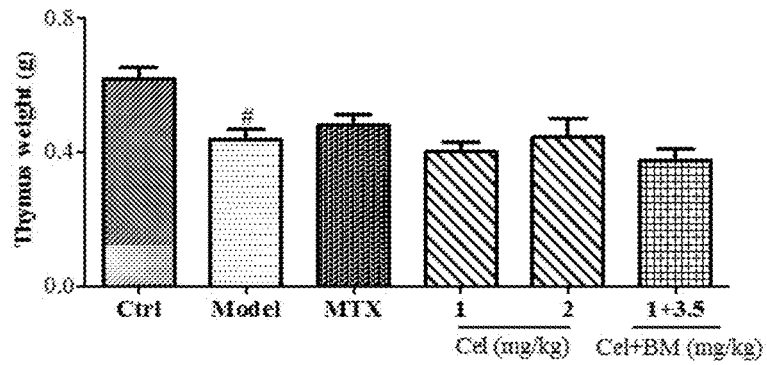
Figure 17I:
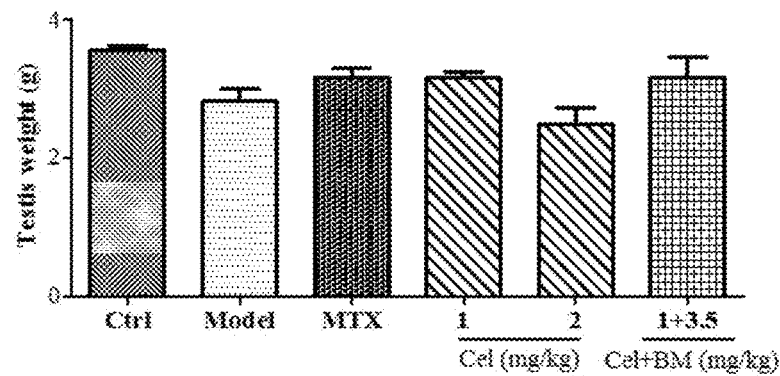

According to the results in FIGS. 15A and 15B, the in vivo efficacy of celastrol via SERCA inhibition was further validated in AIA rat model. Celastrol significantly reduced arthritic scores and hind paw volume in comparison with vehicle-treated AIA rats, without impairment to the body weight or organ weight, FIGS. 16 and 17.

Figure 18:
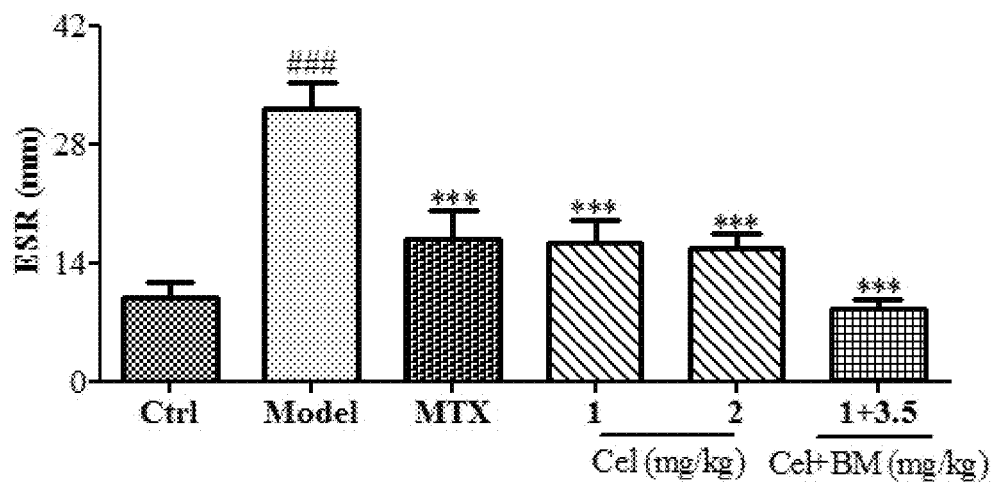
FIG. 18 is a bar chart showing the inflammatory factor, erythrocyte sedimentation rate (ESR) of AIA rats in response to celastrol or positive control drug, MTX treatment.

Apparently, addition of calcium chelator, BAPTA/AM retarded the anti-arthritic effect of celastrol, FIGS. 15A and 15B. With reference to FIG. 18, the inflammatory indicator, erythrocyte sedimentation rate (ESR) also down-regulated upon celastrol and MTX treatment in AIA model.

Figure 19:
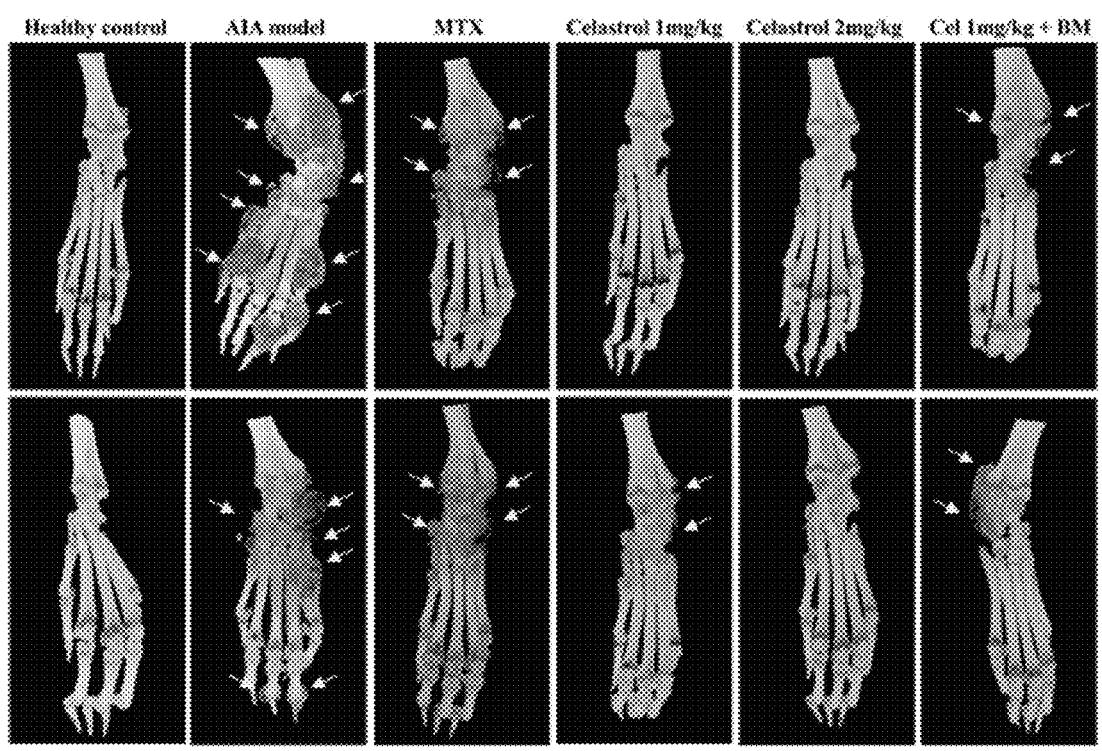
FIG. 19 shows the representative microCT images of the recovery of hind joints from inflammatory destruction in AIA rats after treatment.

In microCT analysis, as shown in FIG. 19, severe swollen joints and cartilage destruction was observed in the AIA model, these inflammatory condition were markedly improved after MTX and celastrol treatment, whereas AIA model treated with celastrol plus BAPTA/AM demonstrated swollen joint and bone damage compared with celastrol treatment alone. Taken together, the results suggest that the anti-arthritic effect of celastrol may be due to SERCA inhibition and calcium mobilization.

The invention claimed is:

1. A method of treating a subject suffering from apoptosis-deficient refractory rheumatoid arthritis, wherein the subject harbors a p53 mutant and is resistant against methotrexate, the method comprising the step of administering an effective amount of a quinonemethide triterpenoid or a pharmaceutically tolerable salt, solvate or anhydrate thereof to the subject, wherein the quinonemethide triterpenoid has a structure of Formula (I):

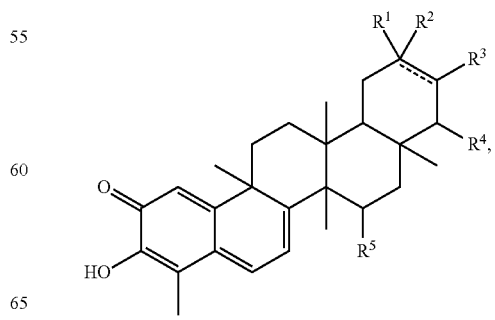

Formula (I)

wherein

- - - - - represents a single or double bond;

$R^1$ is selected from —CH₃, —CH₂OH, —OH or —H;

$R^2$ is selected from —CH₃, —CH₂OH, —OH, —COOH, —COOCH₃, =CH₂ or —H;

$R^3$ is selected from —OH, =O or —H;

$R^4$ is selected from —OH or —H;

$R^5$ is selected from —OH or —H.

2. The method of claim 1, wherein the quinonemethide triterpenoid has a structure of Formula (II):

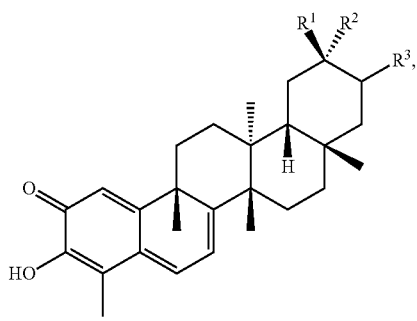

Formula (II)

wherein $R^1$ is selected from —CH₃, or —CH₂OH;

$R^2$ is selected from —COOH or —COOCH₃;

$R^3$ is selected from —OH, =O or —H.

3. The method of claim 1, wherein the quinonemethide triterpenoid has the structure of Formula (IIIa):

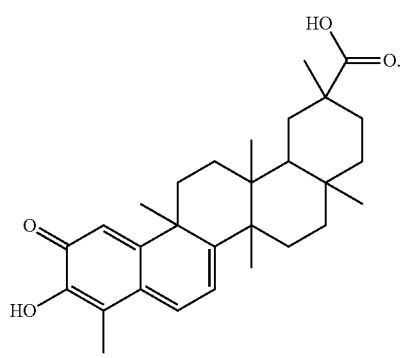

Formula (IIIa)

4. The method of claim 3, wherein the quinonemethide triterpenoid has the structure of Formula (IIIb):

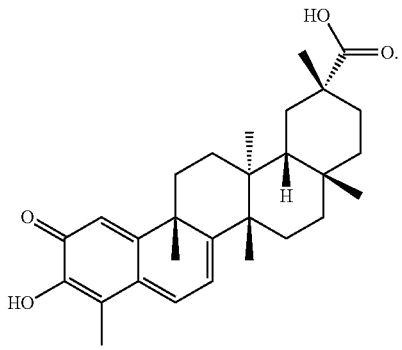

Formula (IIIb)

5. The method of claim 1, wherein the quinonemethide triterpenoid is administered in combination with an effective amount of at least one anti-arthritis compound, which anti-arthritis compound is a compound selected from the group consisting of methotrexate, dexamethasone, prednisolone, abatacept, adalimumab, chloroquinem etanercept, golimumab, infliximab, leflunomide, rituximab, sulfasalazine, colchicine, or a derivative thereof.

6. The method of claim 5, wherein the quinonemethide triterpenoid has a structure of Formula (IIIa) or (IIIb):

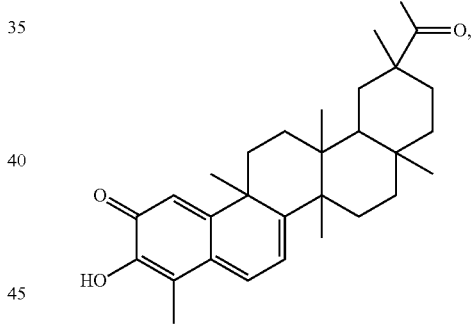

Formula (IIIa)

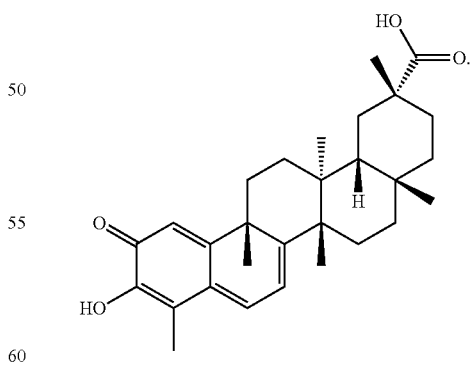

Formula (IIIb)

7. The method of claim 4, wherein the anti-arthritis compound is administered simultaneously with the quinonemethide triterpenoid.

8. A method of inducing autophagy in an apoptosis-deficient rheumatoid arthritis synovial fibroblast harboring a p53 mutant and being resistant against methotrexate, the method comprising the step of contacting at least a population of apoptosis-deficient rheumatoid arthritis synovial fibroblasts with a quinonemethide triterpenoid or a salt, solvate or anhydrate thereof, wherein the quinonemethide triterpenoid has a structure of Formula (I):

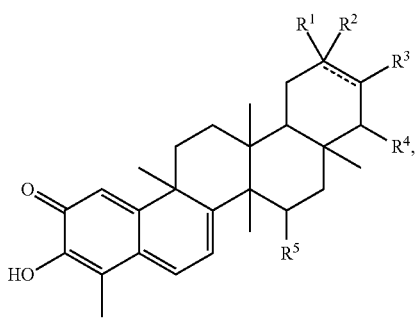

Formula (I)

wherein
= represents a single or double bond;
R¹ is selected from —CH₃, —CH₂OH, —OH or —H;
R² is selected from —CH₃, —CH₂OH, —OH, —COOH, —COOCH₃, =CH₂ or —H;
R³ is selected from —OH, =O or —H;
R⁴ is selected from —OH or —H;
R⁵ is selected from —OH or —H.

9. The method of claim 8, wherein the quinonemethide triterpenoid has a structure of Formula (IIIa) or (IIIb):

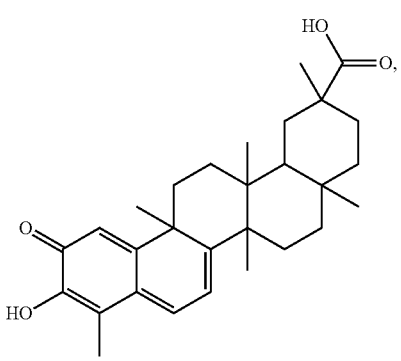

Formula (IIIa)

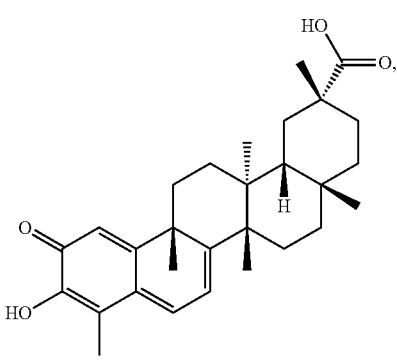

Formula (IIIb)

and wherein the synovial fibroblasts are contacted with between 0.1 µM and 2 µM of said quinonemethide triterpenoid.

10. A method of inducing calcium mobilization in an apoptosis-deficient rheumatoid arthritis synovial fibroblast harboring a p53 mutant and being resistant against methotrexate, the method comprising contacting a population of apoptosis-deficient rheumatoid arthritis synovial fibroblasts with a quinonemethide triterpenoid or a salt, solvate or anhydrate thereof, wherein the quinonemethide triterpenoid has a structure of Formula (I):

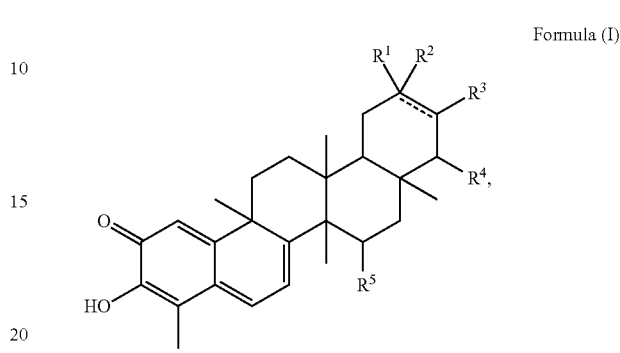

Formula (I)

wherein
= represents a single or double bond;
R¹ is selected from —CH₃, —CH₂OH, —OH or —H;
R² is selected from —CH₃, —CH₂OH, —OH, —COOH, —COOCH₃, =CH₂ or —H;
R³ is selected from —OH, =O or —H;
R⁴ is selected from —OH or —H;
R⁵ is selected from —OH or —H.

11. The method of claim 10, wherein the quinonemethide triterpenoid has a structure of Formula (IIIa) or (IIIb):

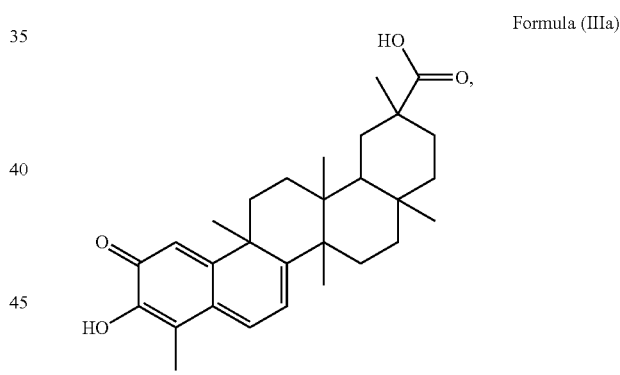

Formula (IIIa)

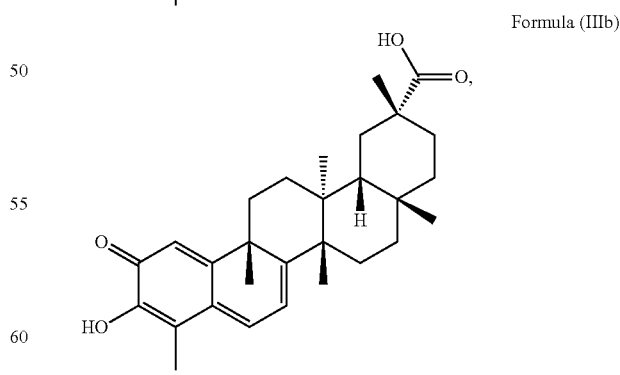

Formula (IIIb)

and wherein the synovial fibroblasts are contacted with between 0.1 µM and 2 µM of said quinonemethide triterpenoid.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthesized sequence

<400> SEQUENCE: 1
atgtacagtg gctccgttcc                                            20

<210> SEQ ID NO 2
<211> LENGTH: 20
<212> TYPE: DNA
<213> ORGANISM: Artificial Sequence
<220> FEATURE:
<223> OTHER INFORMATION: Synthesized sequence

<400> SEQUENCE: 2
acacggctgt tgtcaccata                                            20
```